US011530239B2

(12) United States Patent
Kem et al.

(10) Patent No.: US 11,530,239 B2
(45) Date of Patent: *Dec. 20, 2022

(54) METHODS AND COMPOSITIONS FOR TREATING DISEASES AND CONDITIONS ASSOCIATED WITH GONADOTROPIN RELEASING HORMONE RECEPTOR

(71) Applicant: The Board of Regents of the University of Oklahoma, Norman, OK (US)

(72) Inventors: David C. Kem, Edmond, OK (US); Xichun Yu, Edmond, OK (US); Hongliang Li, Oklahoma City, OK (US); LaTasha B. Craig, Edmond, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 28 days.

This patent is subject to a terminal disclaimer.

(21) Appl. No.: 17/192,152

(22) Filed: Mar. 4, 2021

(65) Prior Publication Data
US 2021/0198318 A1 Jul. 1, 2021

Related U.S. Application Data

(63) Continuation of application No. 16/274,944, filed on Feb. 13, 2019, now Pat. No. 10,975,124, which is a continuation of application No. 62/634,324, filed on Feb. 23, 2018.

(51) Int. Cl.
| | | |
|---|---|---|
| C07K 7/06 | (2006.01) | |
| C07K 7/08 | (2006.01) | |
| C07K 14/71 | (2006.01) | |
| C07K 5/10 | (2006.01) | |
| A61P 35/00 | (2006.01) | |
| A61P 5/02 | (2006.01) | |
| A61P 15/08 | (2006.01) | |
| A61K 38/00 | (2006.01) | |

(52) U.S. Cl.
CPC ............... *C07K 7/06* (2013.01); *A61P 5/02* (2018.01); *A61P 15/08* (2018.01); *A61P 35/00* (2018.01); *C07K 5/10* (2013.01); *C07K 7/08* (2013.01); *C07K 14/71* (2013.01); *A61K 38/00* (2013.01)

(58) Field of Classification Search
CPC ... C07K 7/06; C07K 7/08; C07K 9/00; C07K 5/10; C07K 14/71; A61K 38/16; A61K 38/07; A61K 38/10; A61K 38/00; A61K 38/09; A61K 38/08; A61K 38/18
See application file for complete search history.

(56) References Cited

U.S. PATENT DOCUMENTS

| | | | |
|---|---|---|---|
| 7,348,305 B2 | 3/2008 | Kem et al. | |
| 10,975,124 B2* | 4/2021 | Kem | C07K 7/08 |
| 2008/0081765 A1* | 4/2008 | Yoshitani | B41M 5/42 |
| | | | 503/227 |
| 2010/0135948 A1 | 6/2010 | Payne et al. | |
| 2011/0263504 A1 | 10/2011 | Cerami et al. | |
| 2016/0222084 A1 | 8/2016 | Kem | |
| 2018/0291085 A1 | 10/2018 | Kem | |

OTHER PUBLICATIONS

Shobha, et al.; "An Exploratory Survey to Identify the Adolescents with High Risk for Polycystic Ovarian Syndrome (PCOS) and to Find the Effectiveness of an Awareness Programme Among Students of Selected Pre University Colleges of Udupi District," (2014) IOSR Journal of Nursing and Health Science (IOSR-JNHS), vol. 3, Issue 3 Ver. II; pp. 66-69.
Mayo Clinic, Prostate Cancer, pp. 1-4, obtained https://www.mayoclinic.org/diseases-conditions/prostate-cancer/symptoms-causes/syc-20353087?p=1 on Mar. 30, 2020 (Year: 2020), pp. 1-4.
Ndefo, et al.; "Polycystic Ovary Syndrome a Review of Treatment Options with a Focus on Pharmacological Approaches," (2013), P&T, vol. 38, No. 6, pp. 336-355.
Fedorowski, et al.; "Antiadrenergic Autoimmunity in Postural Tachycardia Syndrome," European Society of Cardiology (2017), 19:1211-1219.
Preeclampsia—Symptoms and Causes—Mayo Clinic; downloaded from website www.mayoclinic.org/diseases-conditions/preeclampsia/systems-causes/syc-20355745.
Low, et al.; "Postural Tachycardia Syndrome (POTS),"; J Cardiovasc Electrophysiol. (Mar. 2009), 20(3):352-358.
Sheldon, et al.; "2015 Heart Rhythm Society Expert Consensus Statement on the Diagnosis and Treatment of Postural Tachycardia Syndrome, Inappropriate Sinus Tachycardia, and Vasovagal Syncope," Heart Rhythm (2015), 12(6):e41-e63.
Raj, Satish R.; "Postural Tachycardia Syndrome (POTS)," Circulation (Jun. 11, 2013), 127(23):2336-2342.
Grubb, Blair P.; "Postural Tachycardia Syndrome," Circulation (2008), 117:2814-2817.
Scott, et al.; "Searching for Peptide Ligands with an Epitope Library," Science, New Series, (Jul. 27, 1990); 249(4967):386-390, Abstract.
Guichard, et al.; "Antigenic Mimicry of Natural L-peptides with Retro-inverso-peptidomimetics,"; Proceedings of the National Academy of Sciences USA (Oct. 1994), 91:9765-9769.
Wallukat; et al.; "Patients with Preeclampsia Develop Agonistic Autoantibodies Against the Angiotensin AT1 Receptor," The Journal of Clinical Investigation (1999), 103:945-952.

(Continued)

*Primary Examiner* — Lianko G Garyu
(74) *Attorney, Agent, or Firm* — Dunlap Codding, P.C.

(57) ABSTRACT

The disclosure is directed in non-limiting embodiments to compounds, compositions, and methods of treating conditions and diseases associated with activation of the gonadotropin GnRH receptor (GnRHR), particularly those involving GnRHR activating autoantibodies (GnRHR AAbs). In one non-limiting embodiment, the disease is Polycystic Ovary Syndrome (PCOS). The therapeutic compounds in at least certain embodiments include peptides which at least partially comprise D-amino acids, such as retro-inverso D-amino acid (RID) peptides, which are able to bind with high affinity to GnRHR AAbs.

8 Claims, 14 Drawing Sheets

Specification includes a Sequence Listing.

(56) References Cited

OTHER PUBLICATIONS

Dragun, et al.; "Angiotensin II Type 1-Receptor Activating Antibodies in Renal-Allograft Rejection," The New England Journal of Medicine; (Feb. 10, 2005), 352(6):558-569.
White, et al.; "Preservation of Myocardial β-adrenergic Receptor Signaling Delays the Development of Heart Failure After Myocardial Infarction," Proc. Natl. Acad. Sci. USA (May 9, 2000), 97(10); 5428-5433.
Ungerer, et al.; "Activation of β-Adrenergic Receptor Kinase During Myocardial Ischemia," Circulation Research (1996) 79:455-460.
Cross, et al.; "Overexpression of the Cardiac β2-Adrenergic Receptor and Expression of a β-Adrenergic Receptor Kinase-1 (βARK1) Inhibitor Both Increase Myocardial Contractility but Have Differential Effects on Susceptibility to Ischemic Injury," Circulation Research (1999) 85:1077-1084.
Kem, et al.; "Serum Autoantibodies Directed to the Gonadotropin Releasing Hormone Receptor ECL2 Accurately Identify and Likely are Causative of PCOS," Endocrine Society Exposition, Apr. 1-3, 2017, Orlando, FL.
Su, et al.; "Effects of GnRH Immunization on the Reproductive Axis and Thymulin," Journal of Endocrinology (2015), 226(2):93-102.
Durán-Pastén, et al.; "Castration-Induced Modifications of GnRH-Elicited [Ca2+]i Signaling Patterns in Male Mouse Pituitary Gonadotrophs In Situ: Studies in the Acute Pituitary Slice Preparation," Biology of Reproduction (2013), 88(2):38, 1-11.
Li, H., et al.; "Atrial Tachyarrhythmias induced by the Combined Effects of β1/2-adrenergic Autoantibodies and Thyroid Hormone in the Rabbit," J. Cardiovasc. Trans. Res. (2014), 7:581-589.
Yu, X., et al.; Autoantibody Activation of Beta-Adrenergic and Muscarinic Receptors Contibutes to an "Autoimmune" Orthostatic Hypotension, J Am Soc Hypertens. (Jan. 2012), 6(1):40-47.
Li, et al.; "Inducible Cardiac Arrhythmias Caused by Enhanced β1-adrenergic Autoantibody Expression in the Rabbit," Am J Physiol Heart Circ Physiol (2014), 306:H422-H428.
Li, H, et al.; "Autoimmune Basis for Postural Tachycardia Syndrome," J Am Heart Assoc. (2014), 3(1):e000755.
Li, H., et al.; "Novel Retro-Inverso Peptide Inhibitor Reverses Angiotensin Receptor Autoantibody-Induced Hypertension in the Rabbit," Hypertension (2015), 65(4):793-799.
Li, H.; "Implications of a Vasodilatory Human Monoclonal Autoantibody in Postural Hypotension," Journal of Biological Chemistry (2013), 288(42):30734-30741.
Millar, et al.; "KISS1R: Hallmarks of an Effective Regulator of the Neuroendocrine Axis," Neuroendocrinology (2015), 101:193-210.
Halvorson, Lisa M.; "PACAP Modulates GnRH Signaling in Gonadotropes," Molecular and Cellular Endocrinology (2014), 385:45-55.
Li, H. "Agonistic Autoantibodies as Vasodilators in Orthostatic Hypotension: A New Mechanism," Hypertension (2012) 59(2):402-408.
Gibson-Helm, et al.; "Delayed Diagnosis and a Lack of Information Associated with Dissatisfaction in Women With Polycystic Ovary Syndrome," Journal of Clinical Endocrinology and Metabolism (2017), 102(2):604-612.
Gentry, et al.; "Novel Allosteric Modulators of G Protein-coupled Receptors," Journal of Biological Chemistry (2015) 290(32):19478-19488.
Maggi, et al.; "GnRH and GnRH Receptors in the Pathophysiology of the Human Female Reproductive System," Human Reproduction Update (2016), 22(3):358-381.
Grassi, Angela; "Polycystic Ovary Syndrome—Unique Concerns During Pregnancy and Lactation," Today's Dietitian (2008), 10(12):38.
Broekmans, et al.; "PCOS According to the Rotterdam Consensus Criteria: Change in Prevalence Among WHO-II Anovulation and Association With Metabolic Factors," BJOG (2006), 113(10):1210-1217.
Kem, et al.; "Gonadotropin Releasing Hormone Receptor Autoimmunity in Polycystic Ovary Syndrome," Endo 2019 PCOS Abstract R11-5-18, (Feb. 24, 2017).
U.S. Appl. No. 14/776,855; David C. Kem, filed Sep. 15, 2015; Office Action dated Jan. 23, 2017.
U.S. Appl. No. 14/776,855; David C. Kem, filed Sep. 15, 2015; Amendment and Response filed Jul. 21, 2017.
U.S. Appl. No. 14/776,855; David C. Kem, filed Sep. 15, 2015; Final Office Action dated Dec. 1, 2017.
U.S. Appl. No. 14/776,855; David C. Kem, filed Sep. 15, 2015; Response to Final Office Action filed Apr. 24, 2018.
U.S. Appl. No. 14/776,855; David C. Kem, filed Sep. 15, 2015; Advisory Action dated May 17, 2018.
U.S. Appl. No. 14/776,855; David C. Kem, filed Sep. 15, 2015; Notice of Abandonment dated Jun. 28, 2018.
International Search Report, dated Jan. 14, 2015, in PCT/US2014/28362, filed Mar. 14, 2014.
Written Opinion of the International Searching Authority, dated Jan. 14, 2015, in PCT/US2014/28362, filed Mar. 14, 2014.
U.S. Appl. No. 16/274,944; David C. Kem, filed Feb. 13, 2019; Office Action dated Feb. 5, 2020.
U.S. Appl. No. 16/274,944; David C. Kem, filed Feb. 13, 2019; Amendment and Response to Office Action, filed Mar. 11, 2020.
U.S. Appl. No. 16/274,944; David C. Kem, filed Feb. 13, 2019; Office Action dated Apr. 3, 2020.
U.S. Appl. No. 16/274,944; David C. Kem, filed Feb. 13, 2019; Amendment and Response to Office Action, filed May 7, 2020.
U.S. Appl. No. 16/274,944; David C. Kem, filed Feb. 13, 2019; Amendment and Response to Office Action, filed May 12, 2020.
U.S. Appl. No. 16/274,944; David C. Kem, filed Feb. 13, 2019; Office Action dated May 12, 2020.
U.S. Appl. No. 16/274,944; David C. Kem, filed Feb. 13, 2019; Final Office Action dated Nov. 25, 2020.
U.S. Appl. No. 16/274,944; David C. Kem, filed Feb. 13, 2019; Amendment and Response to Final Office Action, filed Dec. 4, 2020.
U.S. Appl. No. 16/274,944; David C. Kem, filed Feb. 13, 2019; Notice of Allowance dated Dec. 16, 2020.

* cited by examiner

SEQUENCE LISTING

```
<160> NUMBER OF SEQ ID NOS: 39

<210> SEQ ID NO 1
<211> LENGTH: 28
<212> TYPE: PRT
<213> ORGANISM: Homo sapiens

<400> SEQUENCE: 1

Asp Ser Ser Gly Gln Thr Lys Val Phe Ser Gln Cys Val Thr His Cys
1               5                   10                  15

Ser Phe Ser Gln Trp Trp His Gln Ala Phe Tyr Asn
            20                  25

<210> SEQ ID NO 2
<211> LENGTH: 8
<212> TYPE: PRT
<213> ORGANISM: Homo sapiens

<400> SEQUENCE: 2
```

Trp Trp His Gln Ala Phe Tyr Asn
1               5

<210> SEQ ID NO 3
<211> LENGTH: 8
<212> TYPE: PRT
<213> ORGANISM: Homo sapiens

<400> SEQUENCE: 3

Ser Gln Trp Trp His Gln Ala Phe
1               5

<210> SEQ ID NO 4
<211> LENGTH: 8
<212> TYPE: PRT
<213> ORGANISM: Homo sapiens

<400> SEQUENCE: 4

Ser Phe Ser Gln Trp Trp His Gln
1               5

<210> SEQ ID NO 5
<211> LENGTH: 8
<212> TYPE: PRT
<213> ORGANISM: Homo sapiens

<400> SEQUENCE: 5

His Cys Ser Phe Ser Gln Trp Trp
1               5

<210> SEQ ID NO 6
<211> LENGTH: 8
<212> TYPE: PRT
<213> ORGANISM: Homo sapiens

<400> SEQUENCE: 6

Val Thr His Cys Ser Phe Ser Gln
1               5

<210> SEQ ID NO 7
<211> LENGTH: 8
<212> TYPE: PRT
<213> ORGANISM: Homo sapiens

<400> SEQUENCE: 7

Gln Cys Val Thr His Cys Ser Phe
1               5

<210> SEQ ID NO 8
<211> LENGTH: 8
<212> TYPE: PRT
<213> ORGANISM: Homo sapiens

<400> SEQUENCE: 8

Phe Ser Gln Cys Val Thr His Cys
1               5

<210> SEQ ID NO 9
<211> LENGTH: 8
<212> TYPE: PRT
<213> ORGANISM: Homo sapiens

<400> SEQUENCE: 9

Lys Val Phe Ser Gln Cys Val Thr
1               5

<210> SEQ ID NO 10
<211> LENGTH: 8
<212> TYPE: PRT
<213> ORGANISM: Homo sapiens

<400> SEQUENCE: 10

Gln Thr Lys Val Phe Ser Gln Cys
1               5

<210> SEQ ID NO 11
<211> LENGTH: 8
<212> TYPE: PRT
<213> ORGANISM: Homo sapiens

<400> SEQUENCE: 11

Ser Gly Gln Thr Lys Val Phe Ser
1               5

<210> SEQ ID NO 12
<211> LENGTH: 8
<212> TYPE: PRT
<213> ORGANISM: Homo sapiens

<400> SEQUENCE: 12

Asp Ser Ser Gly Gln Thr Lys Val
1               5

<210> SEQ ID NO 13
<211> LENGTH: 8
<212> TYPE: PRT
<213> ORGANISM: Homo sapiens

<400> SEQUENCE: 13

Cys Val Thr His Cys Ser Phe Ser
1               5

<210> SEQ ID NO 14
<211> LENGTH: 4
<212> TYPE: PRT
<213> ORGANISM: Homo sapiens

<400> SEQUENCE: 14

Val Thr His Cys
1

<210> SEQ ID NO 15
<211> LENGTH: 4
<212> TYPE: PRT
<213> ORGANISM: Artificial Sequence
<220> FEATURE:
<223> OTHER INFORMATION: RID version of SEQ ID NO:14
<220> FEATURE:
<221> NAME/KEY: MISC_FEATURE
<222> LOCATION: (1)..(4)
<223> OTHER INFORMATION: Each amino acid is s D-amino acid

<400> SEQUENCE: 15

Cys His Thr Val
1

<210> SEQ ID NO 16
<211> LENGTH: 12
<212> TYPE: PRT
<213> ORGANISM: Homo sapiens -continued

<400> SEQUENCE: 16

Phe Ser Gln Cys Val Thr His Cys Ser Phe Ser Gln
1               5                   10

<210> SEQ ID NO 17
<211> LENGTH: 5
<212> TYPE: PRT
<213> ORGANISM: Homo sapiens

<400> SEQUENCE: 17

Cys Val Thr His Cys
1               5

<210> SEQ ID NO 18
<211> LENGTH: 6
<212> TYPE: PRT
<213> ORGANISM: Homo sapiens

<400> SEQUENCE: 18

Gln Cys Val Thr His Cys
1               5

<210> SEQ ID NO 19
<211> LENGTH: 7
<212> TYPE: PRT
<213> ORGANISM: Homo sapiens

<400> SEQUENCE: 19

Ser Gln Cys Val Thr His Cys
1               5

<210> SEQ ID NO 20
<211> LENGTH: 8
<212> TYPE: PRT
<213> ORGANISM: Homo sapiens

<400> SEQUENCE: 20

Phe Ser Gln Cys Val Thr His Cys
1               5

<210> SEQ ID NO 21
<211> LENGTH: 5
<212> TYPE: PRT
<213> ORGANISM: Homo sapiens

<400> SEQUENCE: 21

Val Thr His Cys Ser
1               5

<210> SEQ ID NO 22
<211> LENGTH: 6
<212> TYPE: PRT
<213> ORGANISM: Homo sapiens

<400> SEQUENCE: 22

Val Thr His Cys Ser Phe
1               5

<210> SEQ ID NO 23
<211> LENGTH: 7
<212> TYPE: PRT
<213> ORGANISM: Homo sapiens

<400> SEQUENCE: 23

Val Thr His Cys Ser Phe Ser
1               5

<210> SEQ ID NO 24
<211> LENGTH: 8
<212> TYPE: PRT
<213> ORGANISM: Homo sapiens

<400> SEQUENCE: 24

Val Thr His Cys Ser Phe Ser Gln
1               5

<210> SEQ ID NO 25
<211> LENGTH: 6
<212> TYPE: PRT
<213> ORGANISM: Homo sapiens

<400> SEQUENCE: 25

Cys Val Thr His Cys Ser
1               5

<210> SEQ ID NO 26
<211> LENGTH: 7
<212> TYPE: PRT
<213> ORGANISM: Homo sapiens

<400> SEQUENCE: 26

Gln Cys Val Thr His Cys Ser
1               5

<210> SEQ ID NO 27
<211> LENGTH: 8
<212> TYPE: PRT
<213> ORGANISM: Homo sapiens

<400> SEQUENCE: 27

Ser Gln Cys Val Thr His Cys Ser
1               5

<210> SEQ ID NO 28
<211> LENGTH: 9
<212> TYPE: PRT
<213> ORGANISM: Homo sapiens

<400> SEQUENCE: 28

Phe Ser Gln Cys Val Thr His Cys Ser
1               5

<210> SEQ ID NO 29
<211> LENGTH: 7
<212> TYPE: PRT
<213> ORGANISM: Homo sapiens

<400> SEQUENCE: 29

Cys Val Thr His Cys Ser Phe
1               5

<210> SEQ ID NO 30
<211> LENGTH: 8
<212> TYPE: PRT
<213> ORGANISM: Homo sapiens

<400> SEQUENCE: 30

Gln Cys Val Thr His Cys Ser Phe
1               5

<210> SEQ ID NO 31
<211> LENGTH: 9
<212> TYPE: PRT
<213> ORGANISM: Homo sapiens

<400> SEQUENCE: 31

Ser Gln Cys Val Thr His Cys Ser Phe
1               5

<210> SEQ ID NO 32
<211> LENGTH: 10
<212> TYPE: PRT
<213> ORGANISM: Homo sapiens

<400> SEQUENCE: 32

Phe Ser Gln Cys Val Thr His Cys Ser Phe
1               5                   10

<210> SEQ ID NO 33
<211> LENGTH: 8
<212> TYPE: PRT
<213> ORGANISM: Homo sapiens

<400> SEQUENCE: 33

Cys Val Thr His Cys Ser Phe Ser
1               5

<210> SEQ ID NO 34
<211> LENGTH: 9
<212> TYPE: PRT
<213> ORGANISM: Homo sapiens

<400> SEQUENCE: 34

Gln Cys Val Thr His Cys Ser Phe Ser
1               5

<210> SEQ ID NO 35
<211> LENGTH: 10
<212> TYPE: PRT
<213> ORGANISM: Homo sapiens

<400> SEQUENCE: 35

Ser Gln Cys Val Thr His Cys Ser Phe Ser
1               5                   10

<210> SEQ ID NO 36
<211> LENGTH: 11
<212> TYPE: PRT
<213> ORGANISM: Homo sapiens

<400> SEQUENCE: 36

Phe Ser Gln Cys Val Thr His Cys Ser Phe Ser
1               5                   10

<210> SEQ ID NO 37
<211> LENGTH: 9
<212> TYPE: PRT
<213> ORGANISM: Homo sapiens

<400> SEQUENCE: 37

Cys Val Thr His Cys Ser Phe Ser Gln
1               5

```
<210> SEQ ID NO 38
<211> LENGTH: 10
<212> TYPE: PRT
<213> ORGANISM: Homo sapiens

<400> SEQUENCE: 38

Gln Cys Val Thr His Cys Ser Phe Ser Gln
1               5                   10

<210> SEQ ID NO 39
<211> LENGTH: 11
<212> TYPE: PRT
<213> ORGANISM: Homo sapiens

<400> SEQUENCE: 39

Ser Gln Cys Val Thr His Cys Ser Phe Ser Gln
1               5                   10
```

METHODS AND COMPOSITIONS FOR TREATING DISEASES AND CONDITIONS ASSOCIATED WITH GONADOTROPIN RELEASING HORMONE RECEPTOR

CROSS-REFERENCE TO RELATED APPLICATIONS/INCORPORATION BY REFERENCE STATEMENT

This application is a continuation of U.S. Ser. No. 16/274,944, filed Feb. 13, 2019; which claims benefit under 35 U.S.C. 119(e) of U.S. Provisional Application Ser. No. 62/634,324, filed Feb. 23, 2018. The entire contents of each of the above-referenced patent application(s) are hereby expressly incorporated herein by reference.

BACKGROUND

Polycystic Ovary Syndrome (PCOS) is a systemic disease characterized by multiple ovarian cysts, infertility, pain, discomfort, and associated metabolic abnormalities including insulin resistant diabetes mellitus, abnormal sex hormone function, hirsutism, and acne. It is considered of unknown etiology and frequently occurs in adolescence. PCOS involves the pituitary-ovarian reproductive organs, resulting in anovulatory infertility in 8-10% of women of reproductive age. Its causation is currently unknown but is associated with abnormal pituitary control and/or release of both luteinizing hormone (LH) and follicle stimulating hormone (FSH), both of which are intimately related to development and release of ova from the ovary in timely fashion for possible fertilization when a viable sperm is in proximity. In this condition, the release of the developing ova is severely impaired and generally is internally reabsorbed without release. The developing follicle continues to be stimulated by this abnormal absence of rupture and release and becomes a persistent and enlarged cyst leading to distortion of the ovarian architecture and further disturbing normal development of subsequent follicles.

This infertility is profound in many conditions leading to heartbreak, frustration, self-recrimination, and marital discord. Current infertility therapies are frustratingly of low success, and current state of the art resides in in vitro fertilization, often requiring a separate donor and emplacement of the embryo. The costs are very high (e.g., $75K for three attempts) and are without guarantee of issue. Moreover, PCOS is not just an issue of infertility, as a significant majority of these women develop a complex syndrome over several years that includes obesity, significant insulin resistance manifested by Type 2 diabetes mellitus, hypertension, and signs of hyper-androgenism (elevation of testosterone and weak androgens) including acne and hirsutism. A smaller subgroup includes women of thin nature despite eating freely yet who do not develop the above-mentioned metabolic syndrome. These women nevertheless share in the infertility and polycystic ovary presentation. This metabolic syndrome that is so prevalent must be treated using multiple dietary and pharmacological approaches. The diabetes has most commonly been treated with metformin with modest improvement, despite the frequent side effects of the medication and its long term inability to cure the disease. Interestingly, in some subjects there is minimal or very modest improvement in the infertility but this is not common. Newer diabetes medications are being tried but have significant costs and are not recognized as more effective than metformin on the infertility. The hypertension is treated with usually more than one antihypertensive agent with their concomitant cost and side effects. The hyper-androgen state is of particular concern for women of all ages but is especially devastating for young women in society. The therapy usually is started too late and or inadequately and consists of birth control pill (BCP) therapy to suppress LH and the use of androgen receptor antagonists with their concurrent side effects and expense. Alterations in gonadotropin releasing hormone (GnRH) or its receptor (GnRHR) have not been successfully associated with causation.

DETAILED DESCRIPTION

Figure 1A:
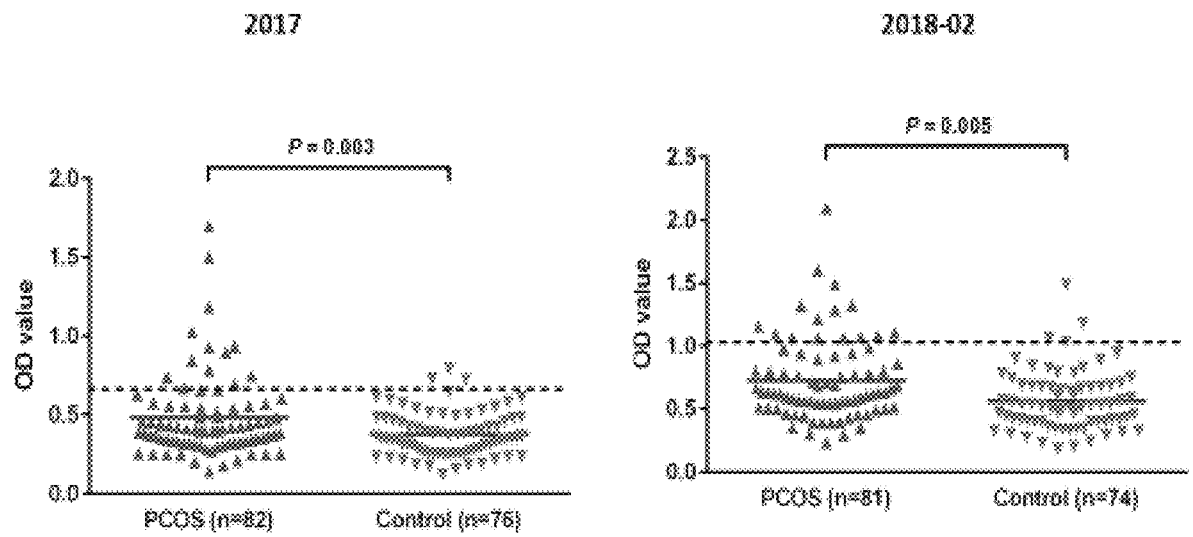
FIG. 1A shows the ELISA O.D. (vertical axis) directed against the GnRHR-extracellular loop 2 (ECL2) sequence for the PCOS for serum from infertile but ovulatory control subjects. The values in the left panel were assayed initially and subsequently repeated after a 5 mo. interval with storage at 4° C. The PCOS values were significantly higher than the controls on both assays, with a p=0.003 and 0.005, respectively. The slight decrease in n for the assay in the second panel was due to insufficient sera in one PCOS subject and two control subjects. The dashed line represents+2 SD of the controls. The solid line is the mean for each group.

The present disclosure is directed, in at least certain embodiments, to compositions and methods of treating conditions and diseases associated with activation of the gonadotropin GnRH receptor (GnRHR), particularly (but not limited to) those involving GnRHR activating autoantibodies (GnRHR AAbs). A particular (but non-limiting) novel feature of the present disclosure is the discovery of the relationship of GnRHR AAbs and Polycystic Ovary Syndrome. Therefore, in at least one embodiment, the present disclosure is directed to treatment of PCOS by the therapeutic clearing of GnRHR AAbs from the circulation. The therapeutic compounds in at least certain embodiments include peptides at least partially comprising D-amino acids, and in further embodiments include retro-inverso D-amino acid (RID) peptides, which are able to bind with high affinity to GnRHR AAbs, thereby inhibiting the binding of the GnRHR AAbs to GnRHR via competitive inhibition.

Without wishing to be bound by theory, it is believed that activating autoantibodies (GnRHR AAbs) which bind to the extracellular loop 2 (ECL2) of GnRHR are produced from an extraneous stimulus (e.g., an infection, stress, etc.) and interact with hypothalamic/pituitary GnRH receptors to inappropriately alter the synthesis and periodic release of LH, leading to hyperandrogenemia, induction of insulin resistance (IR), and metabolic complications.

Before further describing various embodiments of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure. Thus, while the compounds, compositions, and methods of the present disclosure have been described in terms of particular (but non-limiting) embodiments, it will be apparent to those of skill in the art that variations may be applied to the compounds, compositions, and methods, and in the steps or in the sequence of steps of the methods described herein without departing from the concept, spirit, and scope of the inventive concepts.

All patents, published patent applications, and non-patent publications including published articles mentioned in the specification or referenced in any portion of this application, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities, and plural terms shall include the singular. Where used herein, the specific term "single" is limited to only "one."

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1).

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment. Further, all references to one or more embodiments or examples are for purposes of illustration only and are to be construed as non-limiting of the claims.

The term "pharmaceutically acceptable" refers to compounds and compositions which are suitable for administration to humans and/or animals without undue adverse side effects such as (but not limited to) toxicity, irritation, and/or allergic response commensurate with a reasonable benefit/risk ratio. The compounds or conjugates of the present disclosure may be combined with one or more pharmaceutically-acceptable excipients, including carriers, vehicles, and diluents which may improve solubility, deliverability, dispersion, stability, and/or conformational integrity of the compounds or conjugates thereof.

By "biologically active" is meant the ability to modify the physiological system of an organism without reference to how the active agent has its physiological effects.

As used herein, "pure" or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals or subjects within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic or treatment effect in a subject without excessive adverse side effects (such as (but not limited to) substantial toxicity, irritation, and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

The following abbreviations may be used herein for amino acids: alanine:ala:A; arginine:arg:R; asparagine:asn: N; aspartic acid:asp:D; cysteine:cys:C; glutamic acid:glu:E; glutamine:gln:Q; glycine:gly:G; histidine:his:H; isoleucine: ile:I; leucine:leu:L; lysine:lys:K; methionine:met:M; phenylalanine:phe:F; proline:pro:P; serine: ser:S; threonine:thr: T; tryptophan:trp:W; tyrosine:tyr:Y; and valine:val:V.

The term "peptide" is used herein to designate a series of amino acid residues, connected one to the other typically by peptide bonds between the alpha-amino and carbonyl groups of the adjacent amino acids to form an amino acid sequence. In certain embodiments, the peptides can range in length from 4 to 10 to 15 to 25 to 40 to 60 to 75 to 100 amino acids, for example, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids.

The term "polypeptide" or "protein" is used herein to designate a series of amino acid residues, connected one to the other typically by peptide bonds between the alpha-amino and carbonyl groups of the adjacent amino acids, wherein the length is longer than a single peptide. A peptide conjugate refers, in a non-limiting embodiment, to a compound comprising a peptide of the present disclosure which is conjugated (e.g., covalently linked, directly or indirectly via a linker sequence) to another molecule, such as (but not limited to) a carrier molecule such as (but not limited to) a protein or other polymeric molecule, e.g., a serum albumin molecule or antibody, or other therapeutic compound such as (but not limited to) a drug, or an imaging or diagnostic moiety, and wherein the peptide retains its activity (e.g., binding, targeting, imaging, or inhibitory) even when conjugated to the molecule. The peptides of the present disclosure may be produced using any nucleotide sequence which encodes the desired amino acid sequence. Any of the peptides described herein or active variants thereof may be used to make the peptide conjugates of the present disclosure.

Peptides of the present disclosure and the nucleic acids which encode them include peptide and nucleic acid variants which comprise substitutions (conservative or non-conservative) of the native amino acids or bases. For example, the peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein. Examples of such conservative amino acid substitutions may include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met.

One of ordinary skill in the art would readily know how to make, identify, select, or test such variants for receptor targeting activity against the same receptors targeted by the native peptides. Particular examples of conservative amino acid substitutions include, but are not limited to, gly:ala substitutions; val:ile:leu substitutions; asn:glu:his substitutions; asp:glu substitutions; ser:thr:met substitutions; lys: arg:his substitutions; and phe:tyr:trp substitutions. Other types of substitutions, variations, additions, deletions, and derivatives that result in functional variant peptides are also encompassed by the present disclosure, and one of skill in the art would readily know how to make, identify, or select such variants or derivatives, and how to test for receptor binding activity of those variants.

The term "homologous" or "% identity" as used herein means a nucleic acid (or fragment thereof) or a peptide having a degree of homology to the corresponding natural reference nucleic acid or peptide that may be in excess of 60%, or in excess of 65%, or in excess of 70%,or in excess of 75%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%, or other specific percentages described herein. For example, in regard to peptides, the percentage of homology or identity as described herein is typically calculated as the percentage of amino acid residues found in the smaller of the two sequences which align with identical amino acid residues in the sequence being compared, when four gaps per 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

In at least one embodiment, "% identity" represents the number of amino acids or nucleotides which are identical at corresponding positions in two sequences of a peptide or nucleic acids encoding similar peptides. For example, two amino acid sequences each having 15 residues will have at least 60% identity when at least 9 of the amino acids at corresponding positions are the same, at least 66% identity when at least 10 of the amino acids at corresponding positions are the same, at least 73% identity when at least 11 of the amino acids at corresponding positions are the same, at least 80% identity when at least 12 of the amino acids at corresponding positions are the same, at least 86% identity when at least 13 of the amino acids at corresponding positions are the same, and at least 93% identity when at least 14 of the amino acids at corresponding positions are the same. In another example, two amino acid sequences each having 19 residues will have at least 73% identity when at least 14 of the amino acids at corresponding positions are the same, at least 78% identity when at least 15 of the amino acids at corresponding positions are the same, at least 84% identity when at least 16 of the amino acids at corresponding positions are the same, at least 89% identity when at least 17 of the amino acids at corresponding positions are the same, and at least 94% identity when at least 18 of the amino acids at corresponding positions are the same.

Similarly, two amino acid sequences each having 20 residues will have at least 95% identity when 19 of the amino acids at corresponding positions are the same, or at least 90% identity when at least 18 of the amino acids at corresponding positions are the same, or at least 85% identity when at least 17 of the amino acids at corresponding positions are the same, or at least 80% identity when at least 16 of the amino acids at corresponding positions are the same. In other non-limiting examples, two amino acid sequences each having 100 residues will have 95% identity when 95 of the amino acids at corresponding positions are the same. Two amino acid sequences each having 100 residues will have at least 90% identity when at least 90 of the amino acids at corresponding positions are the same. Further, where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%.

Demonstrated for the first time herein is a viable pathophysiology that explains the causation of PCOS and its relationship to onset at a young age in females that are most susceptible to autoimmune issues. It is further believed that this condition afflicts males whose male organs are less susceptible to cyst development but whose androgen and resulting acne and hirsutism may be subject to these influences. Further, a non-genetic form of hypogonadotropic hypogonadism is present in both young and elderly males, caused by such autoantibodies. The relationship of GnRHR-ECL-AAB to the Metabolic Syndrome in 80% of female subjects with PCOS raises the important likelihood that this same relationship exists in some percentage of males who have acquired Metabolic Syndrome. This is a predictable occurrence given that the autoantibodies such as AAb are not a respecter of sexual status other than occurring at a higher percentage of females than males. In summary, this reflects an entirely new direction and course of treatment for PCOS and related issues in hyper-androgenic states that did not exist prior to the therapeutic embodiments of the present disclosure.

In at least certain embodiments, the present disclosure is directed to a peptide comprising 4 to 45 amino acids, wherein the 4 to 45 amino acids comprise a retro-inverso amino acid sequence of SEQ ID NO:15. The peptide may be disposed in a pharmaceutically-acceptable carrier, vehicle, and/or diluent.

In at least certain embodiments, the present disclosure is directed to a peptide comprising 6 to 45 amino acids, wherein the 6 to 45 amino acids comprise an amino acid sequence of SEQ ID NO:14, at least one D-amino acid upstream of the N-terminal end of SEQ ID NO:14, and at least one D-amino acid downstream of the C-terminal end of SEQ ID NO:14. In a particular (but non-limiting) embodiment, the at least one upstream D-amino acid is immediately upstream of the N-terminal end of SEQ ID NO:14, and the at least one downstream D-amino acid is immediately downstream of the C-terminal end of SEQ ID NO:14. The peptide may be disposed in a pharmaceutically-acceptable carrier, vehicle, and/or diluent.

In at least certain embodiments, the present disclosure is directed to a method of treating a disease or condition associated with the gonadotropin releasing hormone receptor, comprising the step of: administering to a subject in need of such therapy at least one of any of the peptides described herein above or otherwise contemplated herein. The peptide may be administered in a composition comprising a pharmaceutically-acceptable carrier, vehicle, and/or diluent. In at least one embodiment of the method, the disease or condition is Polycystic Ovary Syndrome (PCOS). In at least one embodiment of the method, the disease is a condition directly related to (consequent to) Polycystic Ovary Syndrome in males; non-limiting examples of such conditions include (but are not limited to) GnRHR-AAb positive Metabolic Syndrome with abnormal LH, testosterone, insulin resistance, diabetes mellitus, elevated lipids, and elevated cardiovascular risk. In at least one embodiment of the method, the disease or condition is a refractory cancer selected from the group consisting of ovarian, breast, endometrial, uterine, prostate, and testicular cancer.

In at least certain embodiments, the present disclosure is directed to an assay for detecting a gonadotropin releasing hormone receptor activating autoantibody (GnRHR AAb), comprising: a test surface having a peptide bound thereto, the peptide comprising an amino acid sequence of SEQ ID NO:1, or a portion thereof able to bind with high affinity to the GnRHR AAb. The portion of SEQ ID NO:1 may be selected from the group consisting of SEQ ID NOS:1-14 and 16-39.

In at least certain embodiments, the present disclosure is directed to a method of measuring activity of gonadotropin releasing hormone receptor activating autoantibodies (GnRHR AAbs) in a purified serum sample, comprising the steps of: (1) providing a test surface with GnRHR-transfected cells disposed thereon; (2) providing a serum sample suspected of containing GnRHR AAbs, and treating the GnRHR-transfected cells on the test surface with the serum sample in the presence and absence of a GnRHR blocker; (3) measuring GnHRH activity of the treated GnRHR-transfected cells; and (4) comparing the GnHRH activity measured in the GnRHR-transfected cells treated with the serum sample in the presence of the GnRHR blocker to the GnHRH activity measured in the GnRHR-transfected cells treated with the serum sample in the absence of the GnRHR blocker. The GnRHR blocker may be cetrorelix. The GnRHR-transfected cells may be Chem-1 cells.

In certain embodiments, by measuring the direct stimulating activity before and after adding a specific blocker (e.g., cetrorelix), it can be shown that subjects with PCOS have suppressible activity assays while controls do not, thus providing an alternative diagnostic assay to the ELISA. In certain embodiments, by measuring the effect of the AAbs on the stimulating ability of a synthetic GnRHR agonist (e.g., leuprolide), and likely the natural ligand (LHRH) in the activity assay, the GnRHR AAbs enhance the activity of the agonist while control subjects do not show this outcome. This effect can be used to enhance the specificity of the diagnostic assay. Further, by combining the GnRHR-ECL2-AAb ELISA assay results with results of the AMH-ELISA assay described elsewhere herein, specificity of a PCOS diagnostic assay is further enhanced.

In at least one embodiment of the present disclosure, RID peptide homologs (retro-inverso enantiomers comprising D-amino acids in place of the L-amino acids, and in reverse order) based on the core amino acid sequence VTHC (SEQ ID NO:14) can be used to preferentially bind competitively to the GnRHR-AAbs forming a GnRHR-AAb-RID peptide complex, causing the AAb-RID complex to be cleared by the R-E cells lining the liver and the spleen to engulf the complex and eliminate it from the circulation. The RID peptide thus is a decoy peptide that draws down the AAb levels and decreases/eliminates the GnRHR-AAb from reaching and binding to the GnRHR receptor. For example, the RID version of VTHC is represented by $C_D H_D T_D V_D$ (SEQ ID NO:15), where the subscript D represents a D-amino acid, i.e., $C_D$, $H_D$, $T_D$, and $V_D$ are D-amino acid enantiomers of the natural L-amino acids C, H, T, and V.

In at least one embodiment, the RID peptides are 5-10 amino acid residues, and comprise any retro-inverso D-amino acid homolog based on a contiguous sequence of FSQCVTHCSFSQ (SEQ ID NO:16) and which includes at least the RID version of the sequence VTHC, i.e., $C_D H_D T_D V_D$. Examples of L-amino acid sequences derived from FSQCVTHCSFSQ which can be used as templates to form such a RID peptide include, but are not limited to: CVTHC (SEQ ID NO:17), QCVTHC (SEQ ID NO:18), SQCVTHC (SEQ ID NO:19), FSQCVTHC (SEQ ID NO:20), VTHCS (SEQ ID NO:21), VTHCSF (SEQ ID NO:22), VTHCSFS (SEQ ID NO:23), VTHCSFSQ (SEQ ID NO:24), CVTHCS (SEQ ID NO:25), QCVTHCS (SEQ ID NO:26), SQCVTHCS (SEQ ID NO:27), FSQCVTHCS (SEQ ID NO:28), CVTHCSF (SEQ ID NO:29), QCVTHCSF (SEQ ID NO:30), SQCVTHCSF (SEQ ID NO:31), FSQCVTHCSF (SEQ ID NO:32), CVTHCSFS (SEQ ID NO:33), QCVTHCSFS (SEQ ID NO:34), SQCVTHCSFS (SEQ ID NO:35), FSQCVTHCSFS (SEQ ID NO:36), CVTHCSFSQ (SEQ ID NO:37), QCVTHCSFSQ (SEQ ID NO:38), and SQCVTHCSFSQ (SEQ ID NO:39).

The D-amino acid-containing peptides of the present disclosure possess many advantages over the prior art, including but not limited to: (1) the ability to withstand all natural peptidases which can act on peptides comprising L-amino acids; (2) the capability for withstanding gastro-enteric exposure to natural peptidases and to limited acid hydrolysis; and (3) the potential for oral administration.

In another embodiment, the therapeutic peptides of the present disclosure are mixed L-amino acid/D-amino acid peptides which comprises a binding epitope which is constructed of an L-amino acid epitope (e.g., any one of SEQ ID NOS:1-14 and 16-39), while upstream and downstream portions of the peptide comprise one or more flanking D-amino acids on each end of the L-amino acid portion of the peptide. These flanking D-amino acids serve to protect the natural L-amino acid epitope portion of the peptide. For example, this embodiment of a D-amino acid-containing peptide may have the structure:

$$D_1\text{-}L\text{-}D_2$$

wherein "L" represents the specific natural L-amino acid epitope (e.g., any one of SEQ ID NOS:1-14 or 16-39), $D_1$ represents one or more upstream D-amino acids, and $D_2$ represents one or more downstream D-amino acids. For example, but not by way of limitation, each of $D_1$ and $D_2$ may be 1, 2, 3, 4, 5, 6, 7, 8, 9, 10, 11, 12, 13, 14, 15, 16, 17, 18, 19, 20, or more D-amino acids, including any D-amino acid version of the 20 natural L-amino acids.

The compositions of the present disclosure may further contain a conjugate of any of the D-amino acid-containing peptides disclosed, described, or otherwise contemplated herein associated with a labeling agent. Various methods of labeling peptides are known in the art and may be used in accordance with the present disclosure. Examples of labels for polypeptides include, but are not limited to, the following: radioisotopes or radionuclides, fluorescent labels, chemiluminescent labels, and the like. In some embodiments, the labeling agent may be attached to the peptide by a spacer arm of various lengths to reduce potential steric hindrance. In addition, the terms "label," "labeling agent," "detectable marker," "detection moiety," and "reporter molecule" are used interchangeably herein. These conjugates are useful in various diagnostic methods, as discussed in more detail elsewhere herein.

Therapeutic Uses

Peptide compositions of the present disclosure may be administered in therapeutically effective amounts to treat the various conditions identified herein which are associated with the GnRHR, such as (but not limited to) PCOS. An effective amount is a dosage of the composition sufficient to provide a therapeutically or medically desirable result or effect in the subject to which the composition is administered. The effective amount will vary with the particular condition being treated, the age and physical condition of the subject being treated, the severity of the condition, the duration of the treatment, the nature of the concurrent or combination therapy (if any), the specific route of administration, and like factors within the knowledge and expertise of the health practitioner. For example, in connection with methods directed towards treating subjects having a condition characterized by PCOS, an effective amount would be an amount sufficient to mitigate, reduce, modulate, inhibit, or otherwise effectively treat one or more of the conditions in the subject which are associated with PCOS, including (but not limited to) obesity, insulin resistance as manifested by Type 2 diabetes mellitus, hypertension, and hyper-androgenism (elevation of testosterone and weak androgens) including acne and hirsutism.

GnRHRs are known to be present in peripheral tissues of the female reproductive tract, such as (but not limited to) the ovaries and endometrium. Over 50% of resistant tumors of the breast and prostate are also reported to harbor GnRHR. Therefore, in at least certain embodiments, the present disclosure is directed to the treatment of cancers, particularly (but not limited to) refractory cancers, associated with the presence of GnRHR-activating autoantibodies, including (but not limited to) breast, ovarian, endometrial, uterine, testicular, and prostate cancers. This technology permits development of patient selective (precise) therapeutic removal of the deleterious autoantibodies. The AAbs can be cleared from the systemic circulation by the GnRHR AAb-binding peptides described elsewhere herein.

Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount is typically, but not limited to, an amount in a range from 0.1 µg/kg to about 2000 mg/kg, or from 1.0 µg/kg to about 1000 mg/kg, or from about 0.1 mg/kg to about 500 mg/kg, or from about 1.0 mg/kg to about 100 mg/kg, in one or more dose administrations daily, for one or more days. If desired, the effective daily dose of the active compound may be administered as two, three, four, five, six, or more sub-doses, for example, administered separately at appropriate intervals throughout the day, optionally, in unit dosage forms. In some embodiments, the compositions are administered for more than 7 days, more than 10 days, more than 14 days, or more than 20 days. In still other embodiments, the peptide is administered over a period of weeks or months. In still other embodiments, the peptide is delivered on alternate days, for example, the agent may be delivered every two days, or every three days, or every four days, or every five days, or every six days, or every week, or every month.

The peptide compositions may be administered alone or in combination with the above-described drug therapies and may be administered by a variety of administration routes. The particular mode selected will depend upon the compound selected, the condition being treated, the severity of the condition, whether the treatment is therapeutic or prophylactic, and the dosage required for efficacy. The methods of the present disclosure, generally speaking, may be practiced using any mode of administration that is medically acceptable, meaning any mode that produces effective levels of the active compounds without causing clinically unacceptable adverse effects. The administration may, for example, be oral, intraperitoneal, intra-cavity such as (but not limited to) rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not be particularly suitable for long term therapy and prophylaxis. In certain embodiments, however, it may be appropriate to administer the compound in a continuous infusion every several days, or once a week, or every several weeks, or once a month. Intravenous or intramuscular routes may be particularly used in emergency situations. Oral administration may be used for prophylactic treatment because of the convenience to the patient as well as the dosing schedule. Likewise, sustained release devices may be useful in certain embodiments for prophylactic or post-surgery treatment, for example.

Particular pharmaceutical formulations of the presently disclosed peptide compositions include, but are not limited to, sterile aqueous or non-aqueous solutions, suspensions, and emulsions. Non-limiting examples of non-aqueous solvents include propylene glycol, polyethylene glycol, vegetable oils such as (but not limited to) olive oil, and injectable organic esters such as (but not limited to) ethyl oleate. Aqueous carriers include water, alcoholic/aqueous solutions, emulsions, or suspensions, including saline and buffered media. Parenteral vehicles include, for example, sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example (but not by way of limitation), antimicrobials, anti-oxidants, chelating compounds, inert gases, and the like. The pharmaceutical compositions may conveniently be presented in unit dosage form and may be prepared by any of the methods well known in the art of pharmacy.

Compositions suitable for oral administration may comprise discrete units, such as (but not limited to) capsules, tablets, and lozenges, each containing a predetermined amount of the peptide composition. Other compositions include suspensions in aqueous liquids or non-aqueous liquids such as (but not limited to) syrup, an elixir, or an emulsion. In yet other embodiments, the particular vehicle is a biocompatible microparticle or implant that is suitable for implantation into the mammalian recipient.

Other embodiments of the peptide compositions include pharmaceutically acceptable compositions which comprise a therapeutically-effective amount of one or more of the compounds described herein, formulated together with one or more pharmaceutically acceptable carriers (additives) and/or diluents. As described in detail below, the pharmaceutically acceptable compositions may be specially formulated for administration in solid or liquid form, including, but not limited to, those adapted for the following: oral administration, for example, aqueous or non-aqueous solutions or suspensions, tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin; intravaginal or intrarectal administration, for example, as a cream or foam; sublingual administration; ocular administration; transdermal administration; or nasal administration.

Some examples of materials which can serve as pharmaceutically-acceptable carriers include, but are not limited to: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

In solid dosage forms of the peptide compositions for oral administration (capsules, tablets, pills, powders, granules, and the like), the compound or compounds may be mixed with one or more pharmaceutically-acceptable carriers, including, but not limited to, sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose, and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as cetyl alcohol, glycerol monostearate, and non-ionic surfactants; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets, and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Liquid dosage forms for oral administration of the peptides include, but are not limited to, pharmaceutically acceptable emulsions, microemulsions, solutions, suspensions, syrups, and elixirs. In addition to the active ingredient, the liquid dosage forms may contain inert diluents commonly used in the art, such as, for example (but not by way of limitation), water or other solvents, solubilizing agents, and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof. Besides inert diluents, the oral compositions can also include adjuvants such as (but not limited to) wetting agents, emulsifying and suspending agents, sweetening, flavoring, coloring, perfuming, and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

EXAMPLES

Examples are provided hereinbelow. However, the present disclosure is to be understood to not be limited in its application to the specific experimentation, results, and laboratory procedures disclosed herein after. Rather, the Examples are simply provided as one of various embodiments and are meant to be exemplary, not exhaustive.

Example 1: Activating Antibodies Directed to the ECL2 of

Gonadotropin Releasing Hormone Receptor are Diagnostic of PCOS

As noted above, PCOS is a systemic disease characterized by ovulatory dysfunction, hyperandrogenism, and polycystic-appearing ovaries on transvaginal ultrasound with prevalence estimates of up to 19% of the female population of reproductive age using the Rotterdam Conference criteria. In ovulatory women, gonadotropin-releasing hormone (GnRH) is released in a pulsatile manner from the hypothalamus resulting in pulsatile secretion of both LH and FSH, which then communicate with the ovaries to result in ovulation. In contrast, PCOS is characterized by a variable and erratic elevation of LH of unknown etiology. PCOS is also associated with significant metabolic sequelae that lead to other significant long-term healthcare issues noted above.

The present work was based on a hypothesis that GnRHR activating antibodies directed to the ECL2 of GnRHR type 1, a G-protein coupled receptor, would be present in PCOS patients, would contribute to its pathophysiology including erratic LH secretion and downstream effects, and possess diagnostic value.

Methodology

This study was approved by the University of Oklahoma Health Sciences Center Institutional Review Board as conforming to the overlying principles operative in the United States.

Clinical Subjects: Infertile PCOS subjects based on Rotterdam criteria and infertile ovulatory controls seen at an academic infertility clinic 2012-2016 were included in the study if they had stored serum prior to beginning fertility treatment. The PCOS subjects were diagnosed based on 2 of the 3 Rotterdam criteria (ovulatory dysfunction, clinical or laboratory evidence of hyperandrogenism, and/or polycystic appearing ovaries on transvaginal ultrasound) while ruling out other causes of ovulatory dysfunction (i.e. hypothyroidism, hyperprolactinemia). The control patients were infertile ovulatory patients being seen for infertility in the same clinic from 2012-2016. 80 PCOS patients were first identified, and then controls were chosen as 1:1 match for race/ethnicity, age±3 years, and BMI±5. However, controls were excluded if there was no stored serum from initial consultation prior to beginning infertility treatment. Patients underwent a blood draw at their initial consultation for routine infertility evaluation. Separated serum was frozen and stored at −80° C. This serum was de-identified and sent frozen to the laboratory.

Preparation of Specimens: Sera stored at −80° C. were thawed the day prior to assay in a 4° C. refrigerator. When indicated, IgG was purified from 0.5 ml sera using ion exchange chromatography (Pierce NAb Protein A/G Spin Kit, Thermo Scientific, Radnor, Pa.). Protein content was estimated using spectroscopy at 104 nm and normalized to mcg/ml to standardize dosage effects. This IgG was used to demonstrate that the observed activity was related to the autoantibodies and not to other serum components.

Laboratory Assays: ELISA was performed using a 28-mer peptide having the amino acid sequence SEQ ID NO:1 (DSSGQTKVFSQCVTHCSFSQWWHQAFYN) corresponding to the amino acid sequence of the ECL2 of human GnRHR type I. This peptide was synthesized and purified to 95% at GenScript (Piscataway, N.J.) and used to coat 96-well (and subsequently 384-well) ELISA plates overnight at a concentration of 10 μg/mL in a coating buffer at 4° C. Sera were diluted 1:50 with buffer and added to the wells with incubation overnight at 4° C. The following morning, goat anti-human IgG conjugated with alkaline phosphatase (1:2000) was added to the wells and incubated for two hours at 4° C. The substrate para-nitrophenylphosphate 104 was then added to quantify antibody binding. The optical density (OD) values were read at 405 nm at 60 min using a HIDEX Sense ELISA photodensity reader. Data were expressed in OD units comparing the various subgroups.

Cell-based GnRHR-AAb Activity Assays: Activity of GnRHR AAb in IgG purified from sera of subjects with PCOS and controls were analyzed with a GnRHR-transfected Chem-1 cell-based calcium flux assay (Eurofins Scientific, USA). Briefly, Chem-1 cells were dispensed into 96-well plates and incubated 24 h, after which assay plates were washed sufficiently with Hank's Balanced Salt Solution (HBSS) supplemented with 20 mM HEPES, 2.5 mM Probenecid at pH 7.4 to remove all trace of Media. Component. Serum-derived IgG (0.1 mg/mL) was added in the presence and absence of the non-selective GnRHR blockade. Samples were tested in triplicate. FLUO-8®, AM $Ca^{2+}$ dye (Cat No: 21080, AAT Bioquest, Inc., Sunnyvale, Calif.) was prepared by dissolving 1 mg of Fluo-8 NW in 200 of DMSO and applied to the assay plate ($Ca^{2+}$ dye at 10 µL/10 mL is sufficient for loading one plate). Excitation wave length was set at 470-495 nm and emission wave length at 515-565 nm for $Ca^{2+}$ dyes. Maximal fluorescence signal was obtained by HIDEX Sense reader.

AMH levels by Gen II ELISA: The Anti-Müllerian hormone (AMIH) Gen II ELISA is an enzymatically amplified two-site immunoassay (BECKMAN COULTER, USA) with units of ng/ml. In the assay, calibrators, controls, and samples were incubated in microtitration wells which have been coated with anti-AMH antibody. After incubation and washing, anti-AMH detection antibody labeled with biotin was added to each well. After a second incubation and washing step, streptavidin-horseradish peroxidase (HRP) was added to the wells. After a third incubation and washing step, the substrate tetramethylbenzidine (TMB) was added to the wells. Lastly, an acidic stopping solution was added. The degree of enzymatic turnover of the substrate was determined by dual wavelength absorbance measurement at 450 nm and between 600 nm and 630 nm. The absorbance measured was directly proportional to the concentration of AMH in the samples. A set of AMH calibrators was used to plot a calibration curve of absorbance versus AMH concentration. The AMH concentrations in the samples can then be calculated from this calibration curve.

Statistical Analysis: Group data are presented as mean±SD or percent. Normally distributed groups were compared using Student t or Pearson chi-squared tests. A ROC curve was used to assess OD as a diagnostic test for PCOS. Significance was assigned to two way values of p<0.05.

Methods Summary: Infertile PCOS subjects based on Rotterdam criteria and infertile ovulatory controls seen at an academic fertility clinic 2012-2016 were included in the study if they had stored serum prior to beginning treatment. Serum was screened by ELISA for AAbs to GnRHR using a synthetic 28-mer peptide from the ECL2 and ECL 1 of human GnRHR as coating antigen. Optical density (OD) values were read at 405 nm at 60 minutes. Activity of GnRHR AAb in sera and in IgG purified from sera of 4 subjects with PCOS and 4 controls was analyzed with a GnRHR-transfected Chem-1 cell-based calcium flux assay. AAb-specific effect was tested by GnRHR blockade. Group data are presented as mean±SD or percent. Groups were compared using Student t or Pearson chi-squared tests. An ROC curve was used to assess OD as a diagnostic test for PCOS.

Results

There were no significant differences in the age of the PCOS subjects and those with non-PCOS related infertility. There was a significant increase in the BMI of the PCOS compared to their control subjects.

Figure 1B:
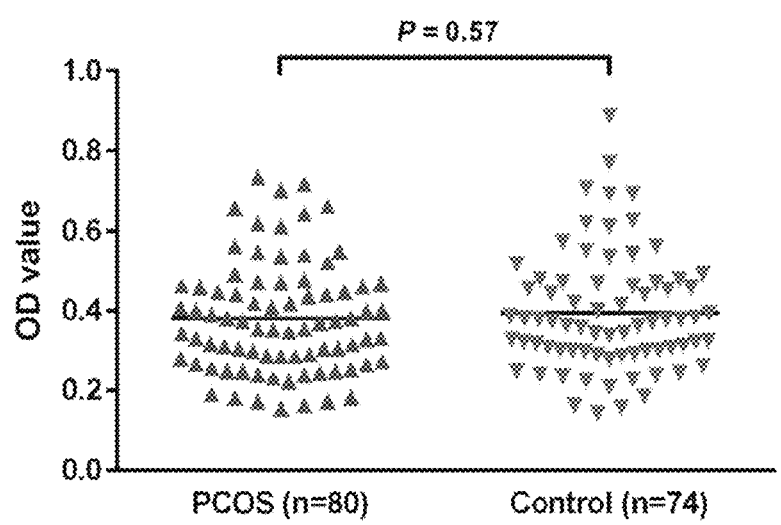
FIG. 1B shows an ELISA assay of these subjects using the GnRHR-ECL1 sequence. There was no evidence for an Ab directed toward this adjacent ECL (extracellular loop).
Figure 1C:
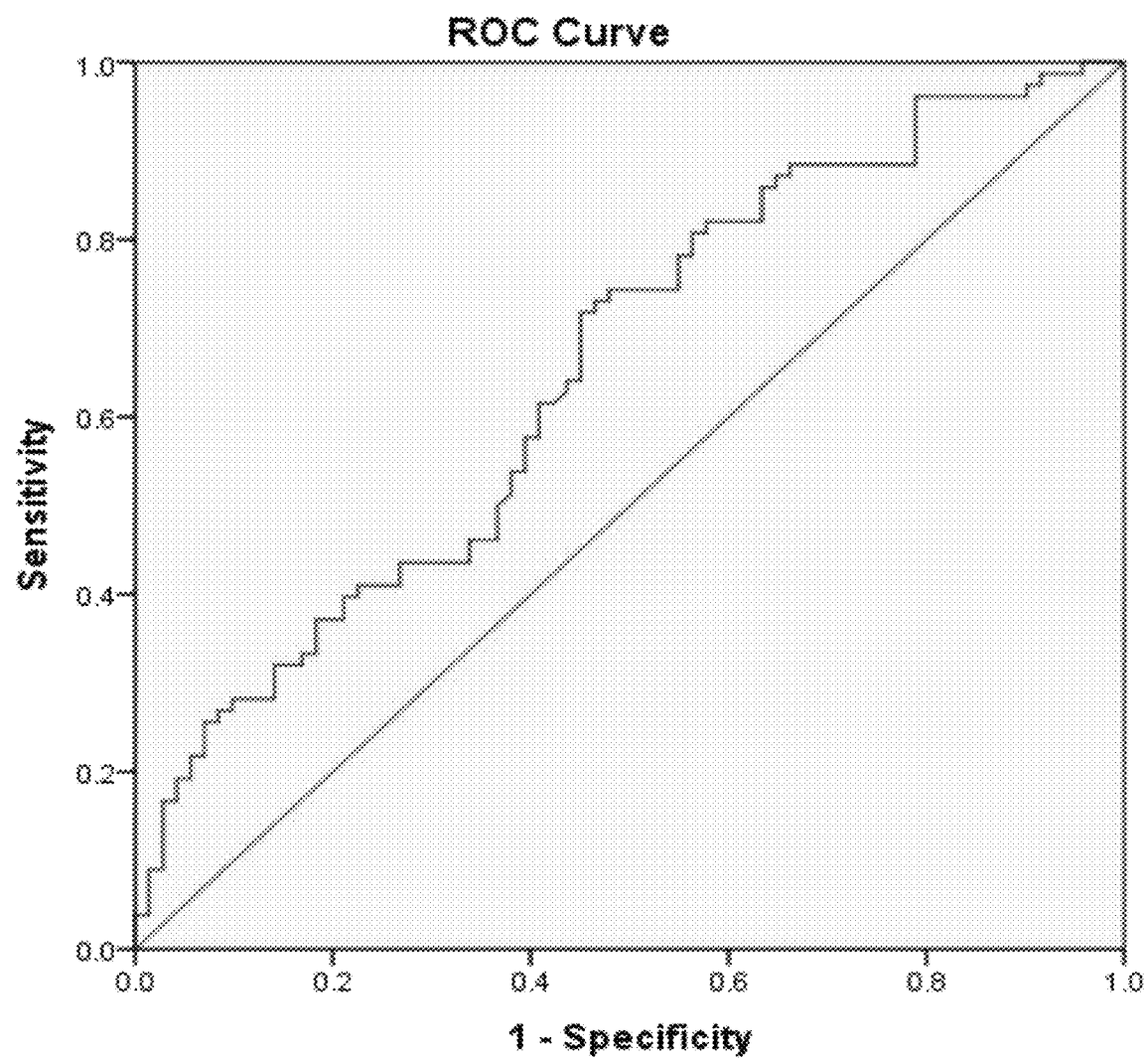
FIG. 1C shows a ROC curve comparing the ELISA OD assayed in the PCOS and control subjects (data are from the right panel of FIG. 1A). There is a sensitivity of 72% and a specificity of 55% compared to a theoretical control population (dashed line). The area under the curve was significantly different from the controls (p=0.0013). Diagonal segments are produced by ties. These were subjects matched for age and BMR and blinded to the lab.
Figure 2A:
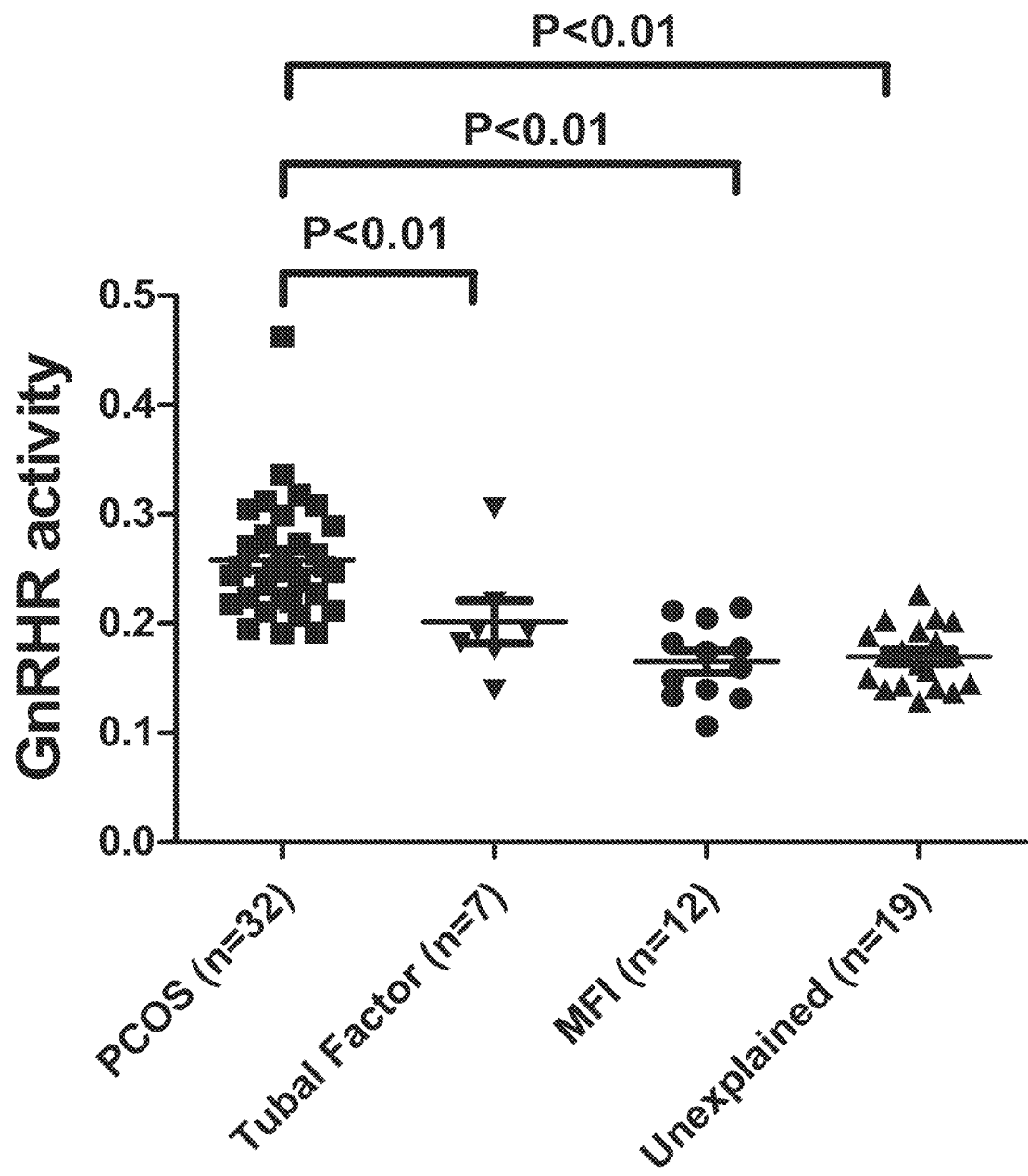
FIG. 2A shows GnRHR-ECL2 ELISA values for a group of 32 PCOS subjects compared to the subtype of infertility in the control subjects. These assays were run on 96 well plates. The control values were significantly lower than the PCOS subjects in each group.
Figure 2B:
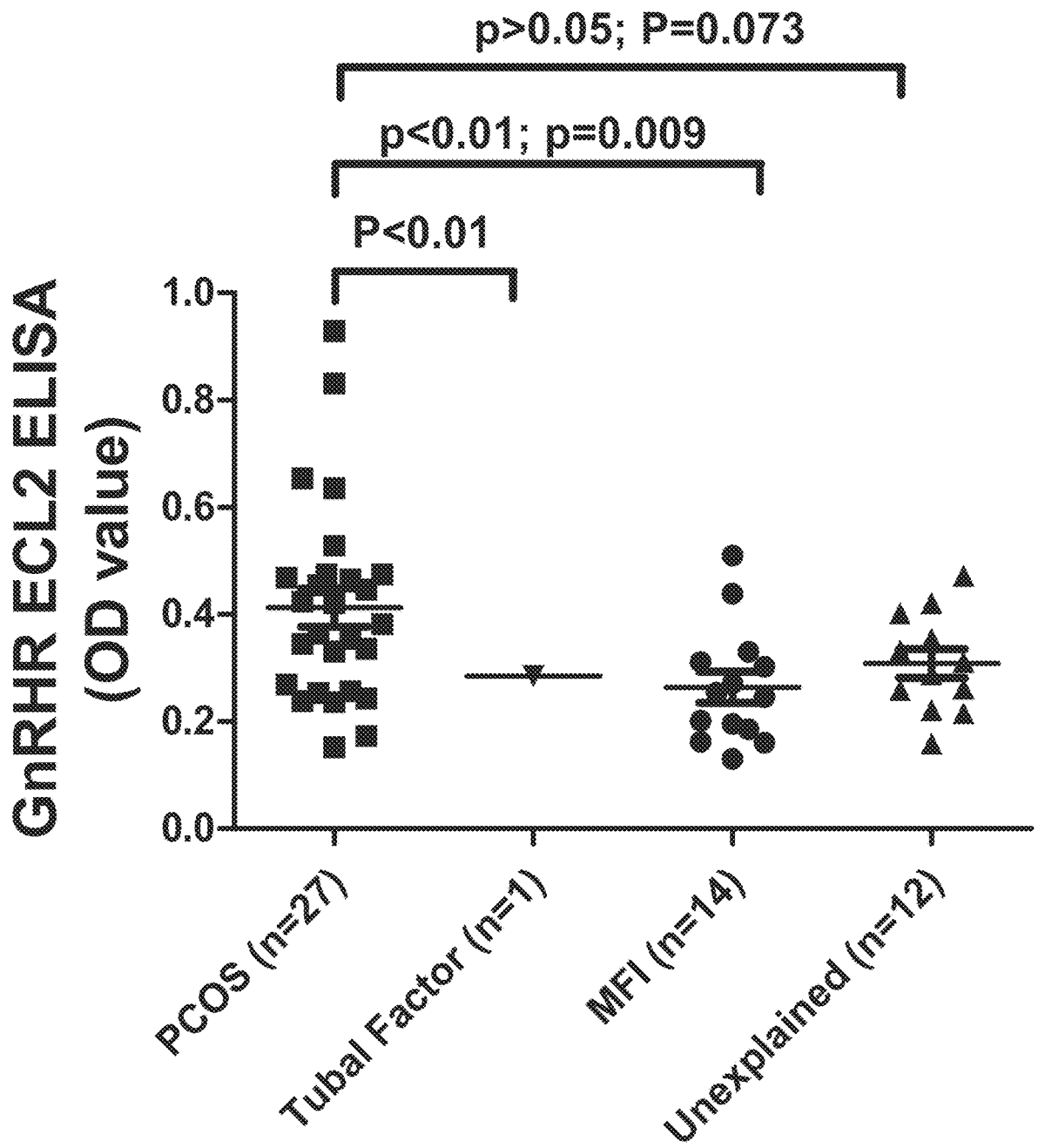
FIG. 2B shows GnRHR-ECL2 ELISA values for a group of 27 PCOS subjects compared to the subtype of infertility in the control subjects. These assays were run on 96 well plates. The control values were significantly lower than the PCOS subjects in each group.

ELISA data: Each PCOS subject's serum initially was assayed by ELISA for antibodies directed toward the hECL-2 and then for ECL1 as described above. These assays were performed in triplicate in 384 well plates to eliminate intra-well variance. The plate included PCOS subjects and their closely age matched infertile but ovulatory control subjects. FIG. 1A demonstrates the ELISA data for the PCOS subjects and controls that were age and BMI matched. There was a significant increase in the GnRHR-ECL2 ELISA OD for the PCOS versus the controls (p<0.003) (left panel). This assay tested sera at a 1/50 dilution, and the resulting OD was read at 60 minutes. A repeat assay was then performed several months later using the same sera stored at 4° C. (right panel). This assay used a 1/25 serum dilution and was read at 30 minutes. These data were virtually identical, with a difference in OD between the PCOS and control groups of p=0.005. These data express the direct orthosteric impact of the sera on the receptor. Although the group's values were significantly different, there was some overlap of a number of PCOS samples with the control group. Anti-Müllerian hormone levels were independently assayed in a subset of these subjects (data not shown). If there was a presence of either or both, there was a higher predictive value for a Dx of PCOS. The ELISA assay for GnRHR-ECL1-AAb for PCOS subjects versus controls is shown in FIG. 1B. There was no evidence for AAb directed toward the ECL1. The ROC curve (FIG. 1C) for the ECL2 data indicate a 72% sensitivity and a 55% specificity. The PCOS values by ELISA were compared to the subgroups of the control ovulatory but infertile subjects, and the PCOS ELISA values were found to be higher (p<0.01) than each of the subgroups of Tubal Factor, Male Factor Infertility (MFI), and Unexplained Infertility (FIGS. 2A and 2B). The combination of the PCOS and anti-Müllerian hormone in the form of a PCOS assay panel provides a superior level of discrimination in the evaluation of infertility and provides a reliable diagnostic assay for PCOS.

Figure 3A:
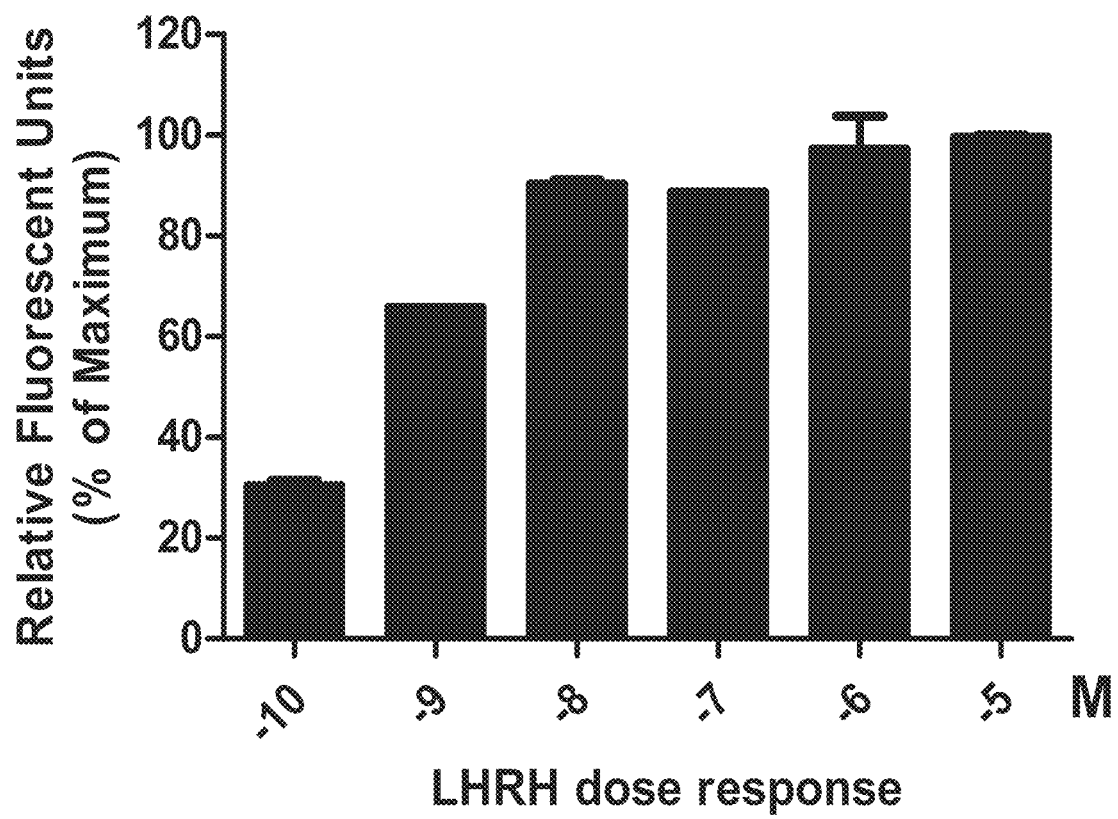
FIG. 3A shows the dosage response curve for the normal ligand hLHRH (human Leutenizing Hormone Releasing Hormone) on relative $Ca^{2+}$ induced Fluo-8 NW fluorescence. The values are expressed as the percentage of maximal fluorescence induced during the exposure period.
Figure 3B:
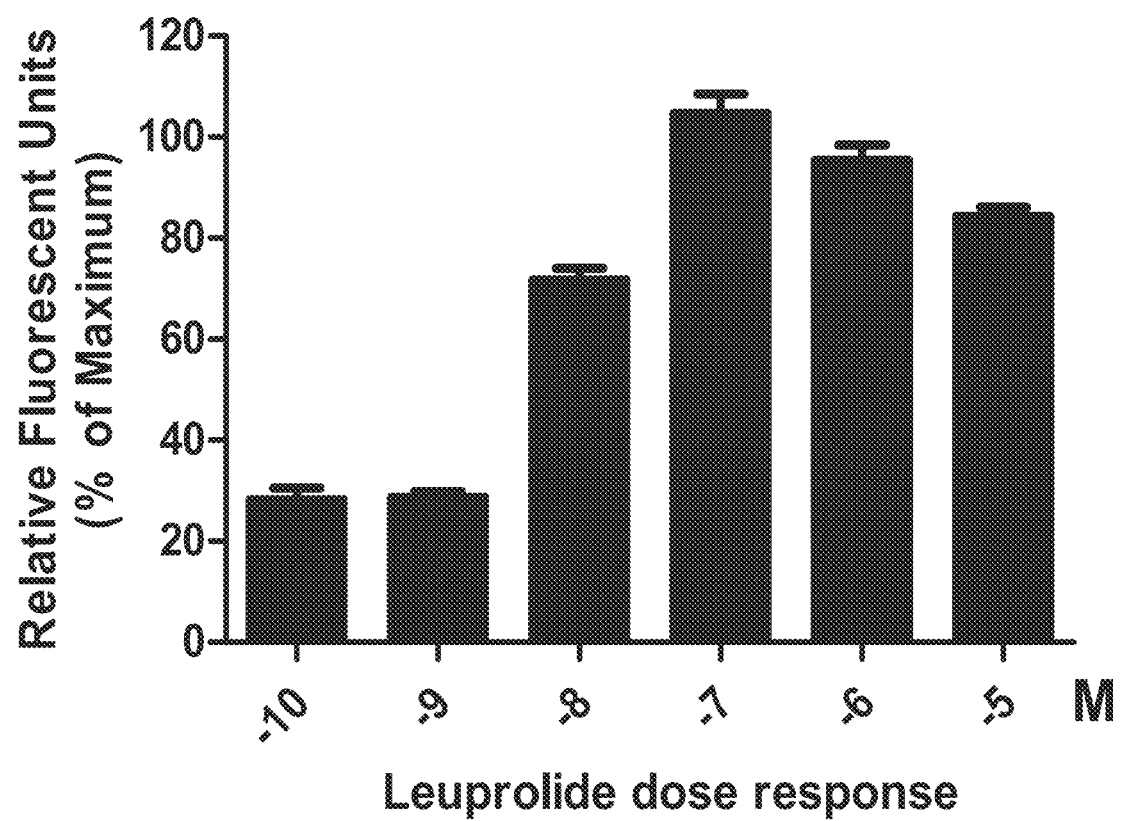
FIG. 3B shows the dosage response curve for the synthetic agonist leuprolide on relative $Ca^{2+}$ induced Fluo-8 NW fluorescence. The values are expressed as the percentage of maximal fluorescence induced during the exposure period. The normal ligand hLHRH (FIG. 3A) and leuprolide demonstrated similar actions at $10^{-9}$ M and $10^{-8}$ M, n=4, respectively.

Activity Assays: GnRHR-transfected cells were used to examine the activity of sera from subjects demonstrating a significant presence of GnRHR-ECL2 Ab on ELISA. FIGS. 3A and 3B demonstrate this assay is sensitive to a dosage of $10^{-9}$ M and above using the normal agonist hLHRH (Fisher, Inc) and at $10^{-8}$ M and higher using the selective agonist leuprolide (LEUPRON®, AbbVie Inc., North Chicago, Ill.).

Figure 4A:
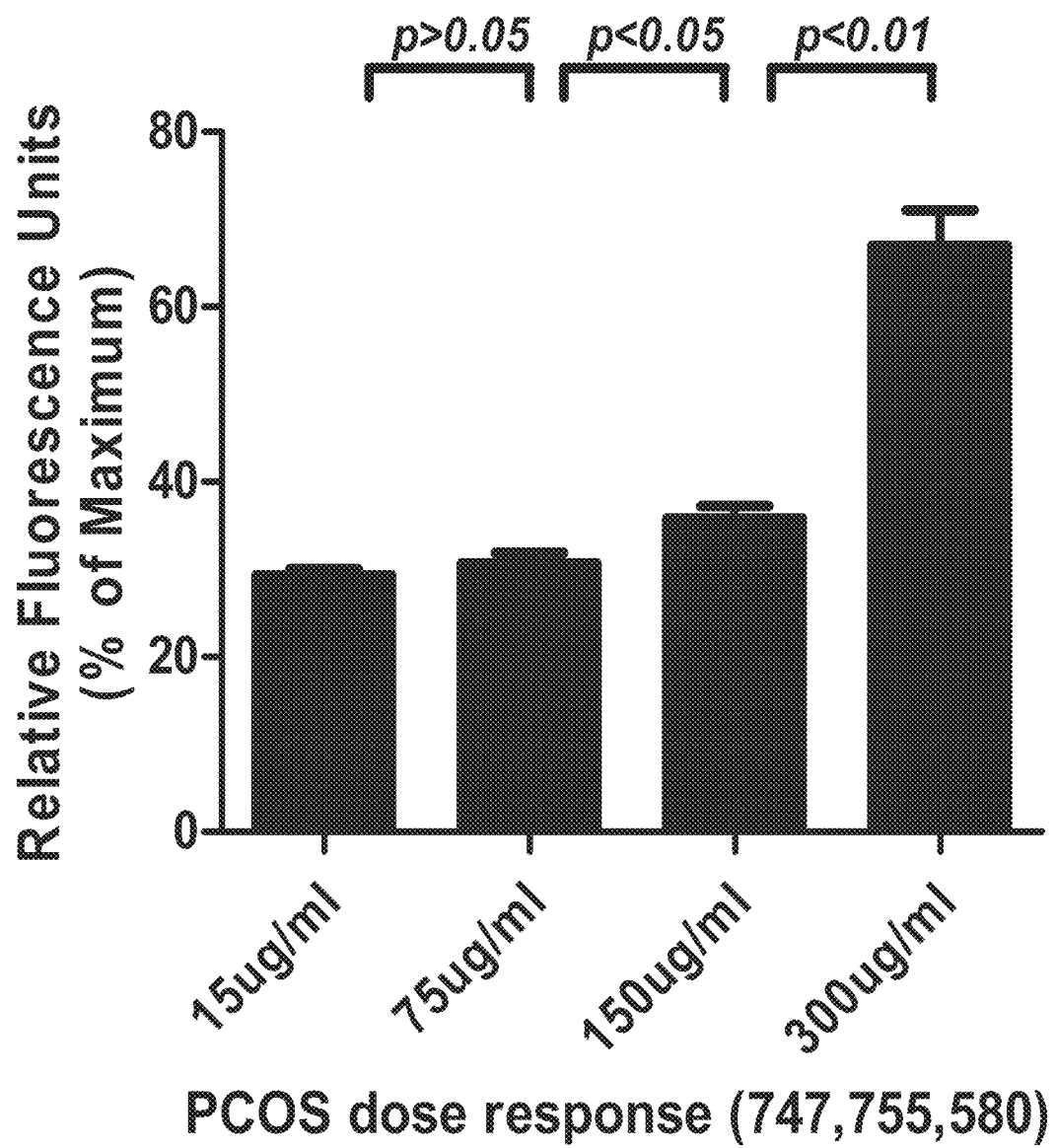
FIG. 4A shows a dosage response curve for IgG derived from 3 subjects with a positive GnRHR-ECL2 ELISA. The significance for each dosage above baseline is shown.
Figure 4B:
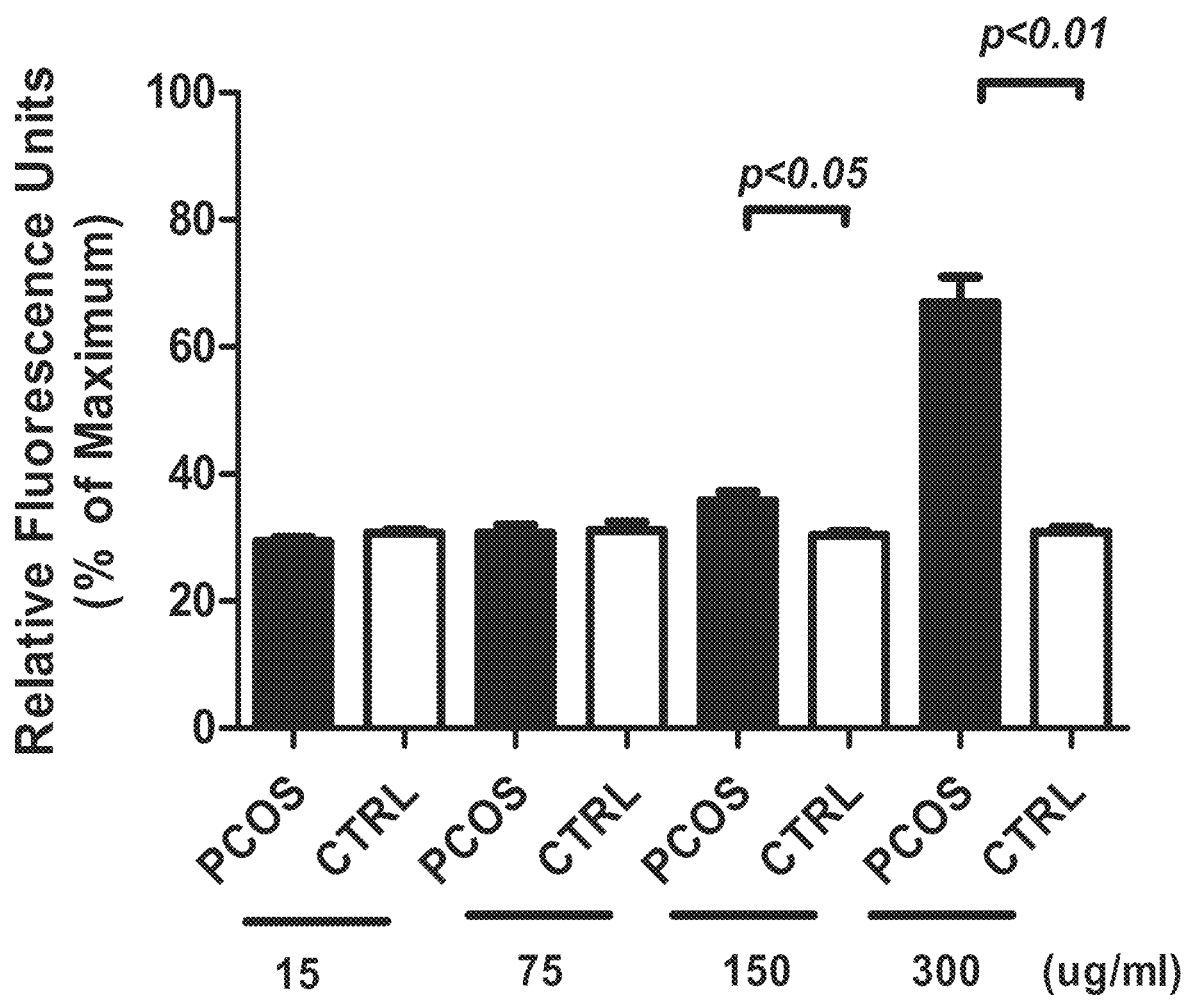
FIG. 4B shows the PCOS response of FIG. 4A compared to IgG from 3 control subjects.

FIGS. 4A and 4B show a composite dosage response curve (15, 75, 150, and 300 mcg/ml of IgG) for IgG purified from serum from three PCOS subjects with elevated GnRHR-ECL2 ELISA values. There was a significant increase in $[Ca^{2+}]_i$ observed at 75, at 150, and most dramatically at 300 mcg/ml in GnRHR-transfected cells.

Figure 5:
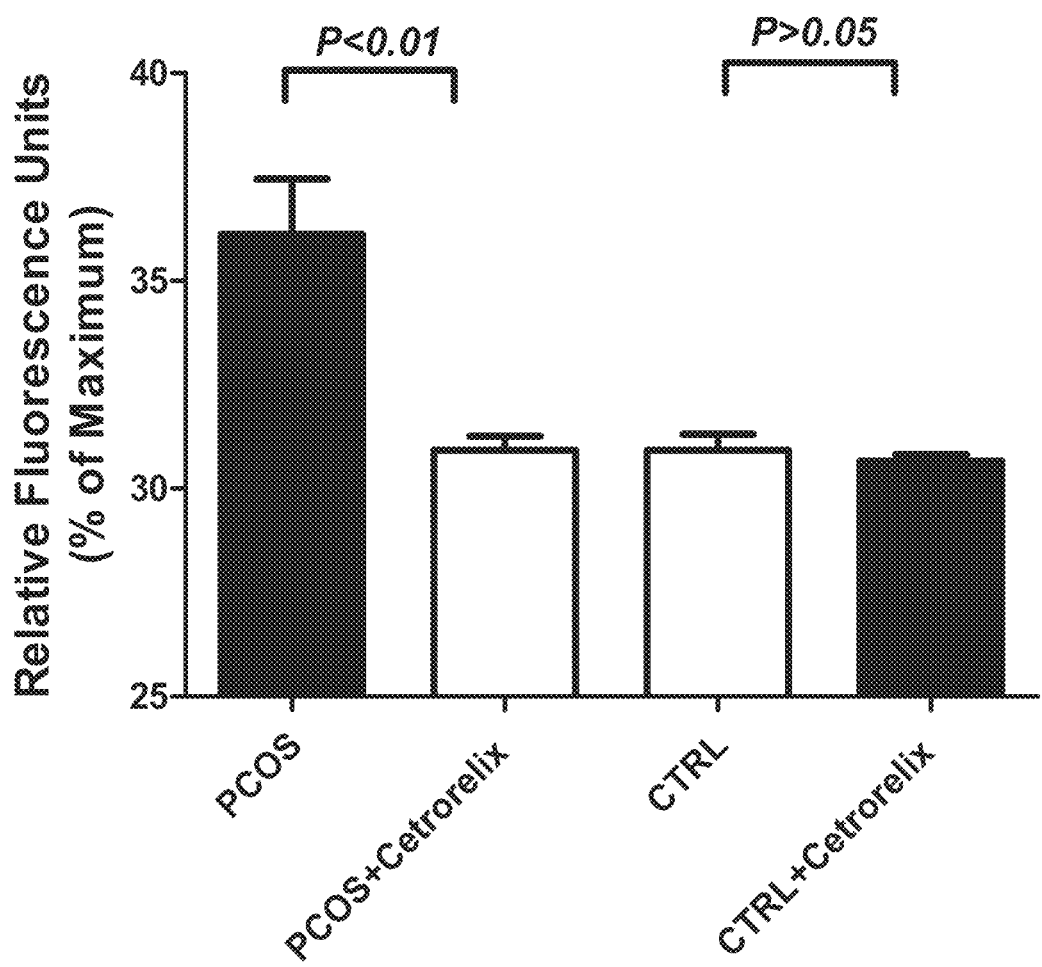
FIG. 5 demonstrates the effect of the GnRHR specific antagonist cetrorelix ($10^{-5}$ M) on the GnRHR activity of 4 subjects with PCOS and their controls. The antagonist suppressed the relative fluorescence expressed as % of maximum fluorescence to baseline while the activity for the controls was not significantly changed.

FIG. 5 demonstrates the effect of the GnRHR activity in the transfected cells following exposure to sera from 3 PCOS subjects and 3 control subjects before and after 2-hour exposure to the specific GnRHR antagonist cetrorelix. There was no significant decrease in activity in the control subjects, while the elevated activity in the PCOS subjects dropped to the values observed in the control patient samples.

Figure 6:
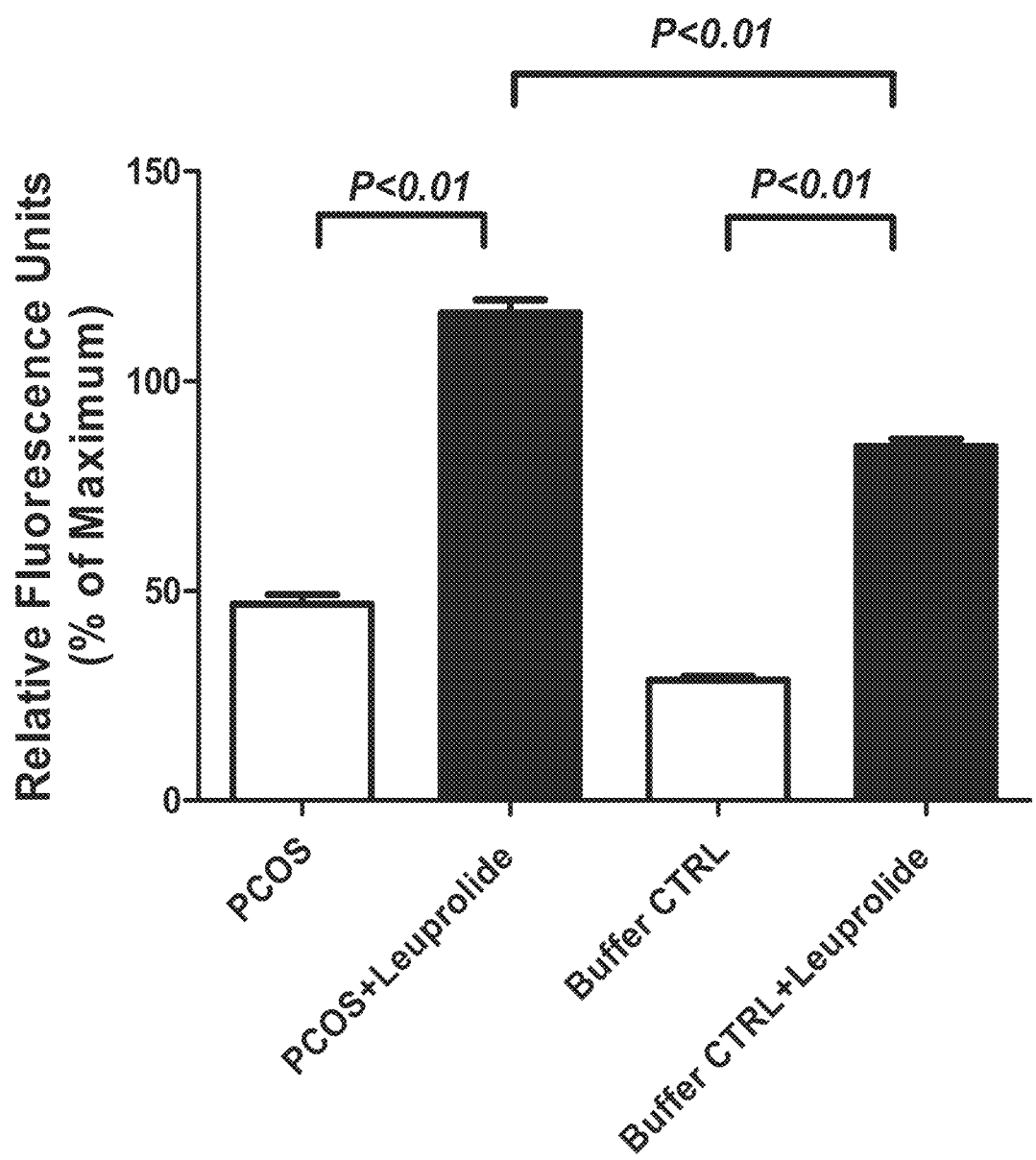
FIG. 6 shows the effect of the GnRHR synthetic agonist leuprolide on the GnRHR transfected cells alone and in the presence of IgG purified from PCOS subjects with active autoantibodies (AAb). The presence of the IgG increased the total activity at least in an additive fashion over the buffer+ leuprolide. (n=4, $p<0.01$).
Figure 7:
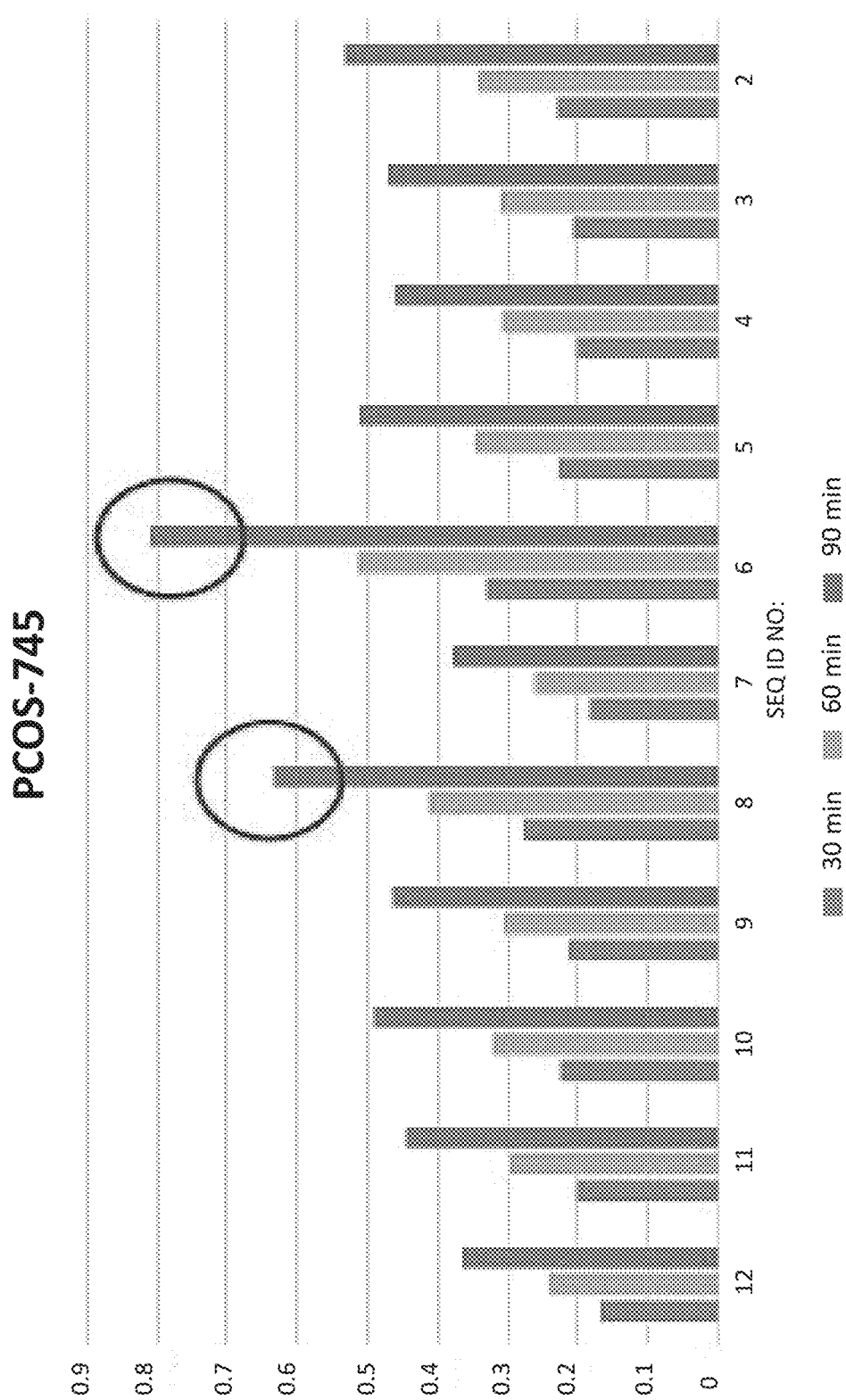
FIG. 7 shows a minipin ELISA using PCOS serum and its interaction with multiple pins containing sequences, each offset by two amino acids, of the GnRHR-ECL2 peptide structure. The peaks represent sites of increased binding by Abs present in the sera. The amino acid sequence for each pin is shown at the bottom. Representative PCOS with 2 dominant peaks. Each color bar represents the time of O.D. reading after addition of chromagen (30, 60, and 90 min).
Figure 8:
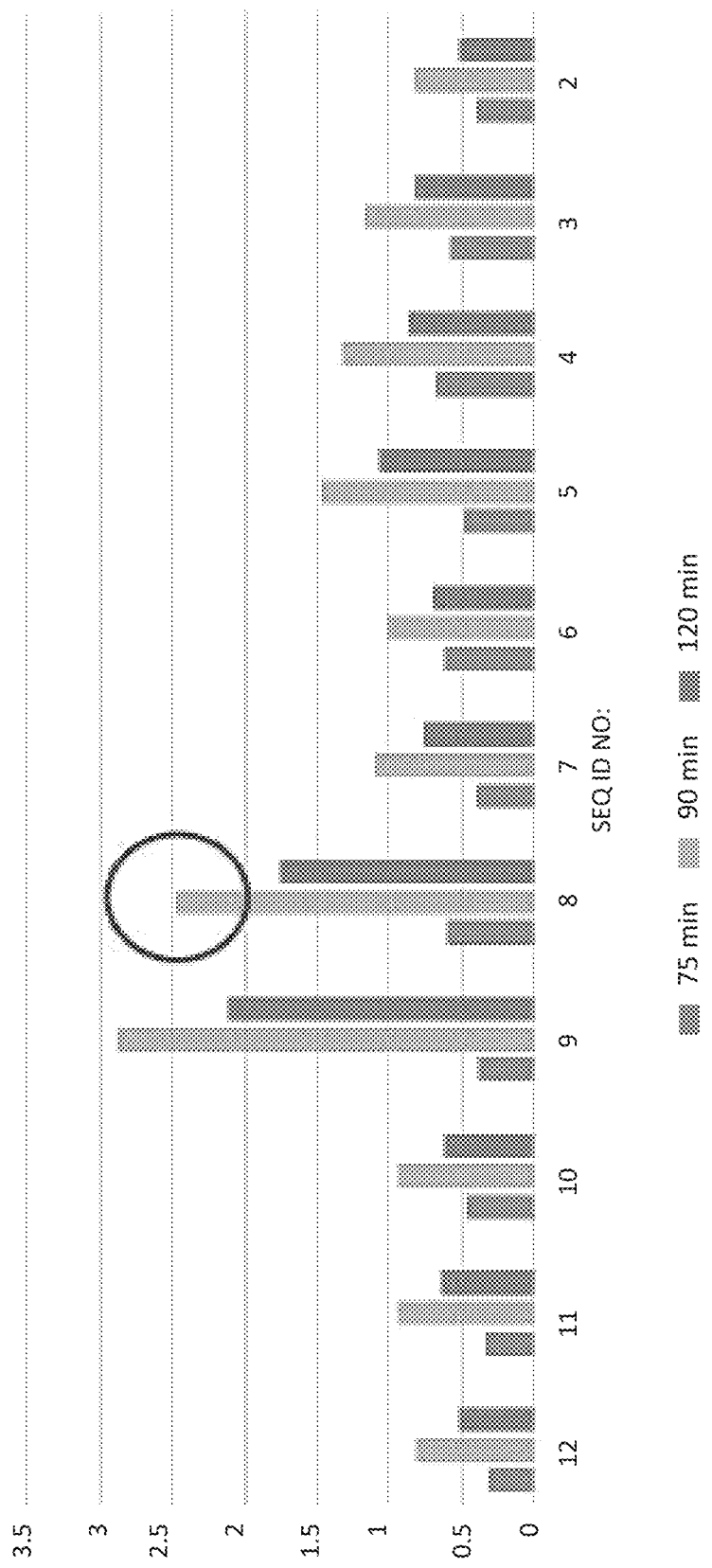
FIG. 8 shows a minipin ELISA using PCOS with a single dominant peak and high O.D. (note different vertical scale for high O.D.).
Figure 9:
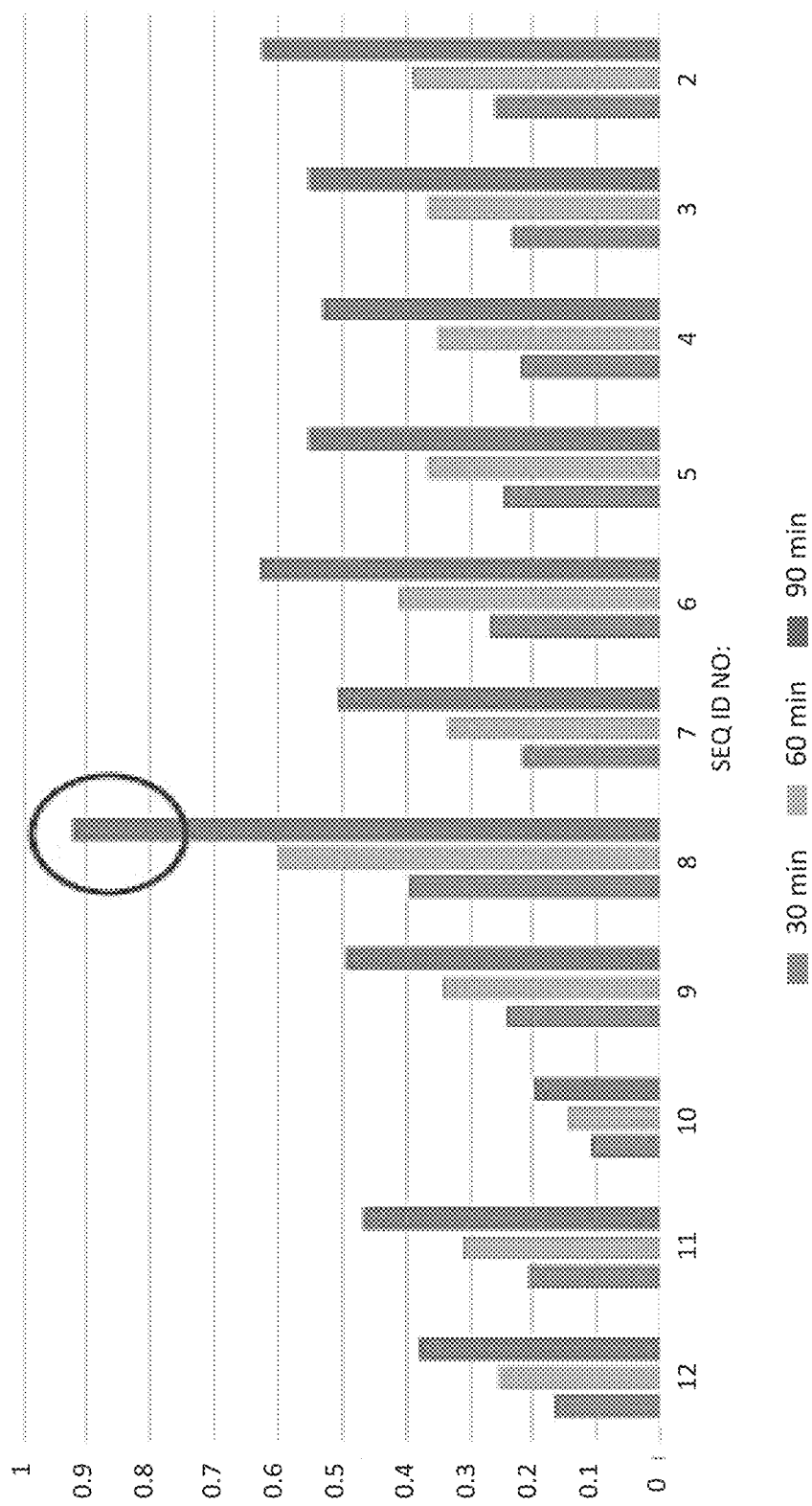
FIG. 9 shows a minipin ELISA of a control with single first peak with moderate O.D. value (note different vertical scale).
Figure 10:
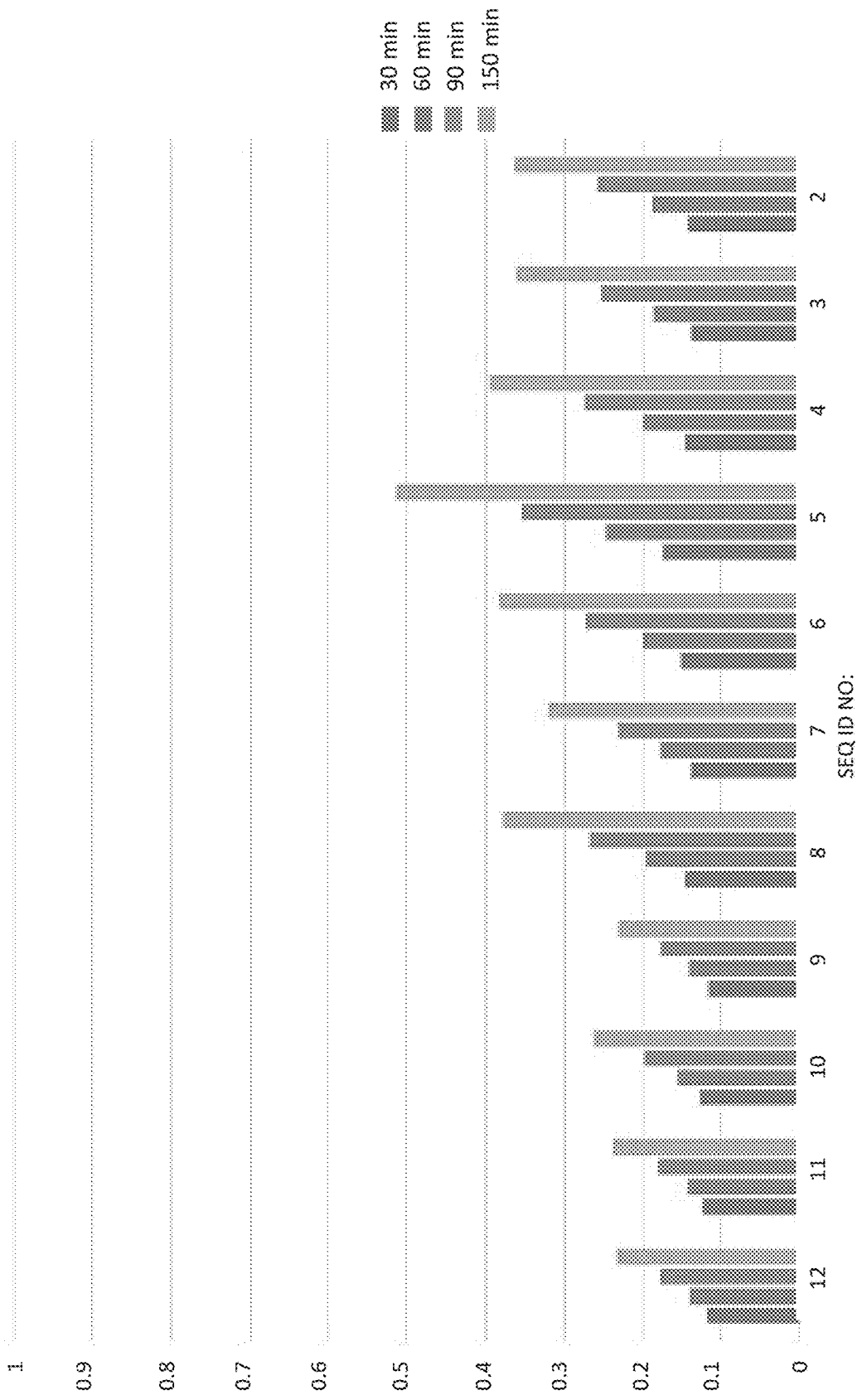
FIG. 10 shows a minipin ELISA of a control with relatively low activity (note low vertical scale compared to FIG. 9).

FIG. 6 demonstrates the effect of the agonist leuprolide on the GnRHR-transfected cell activity with buffer alone and when PCOS sera was added with the agonist. The effect of the sera alone was greater than buffer alone. Sera plus leuprolide was significantly higher than the leuprolide plus buffer. These effects were at least additive.

Results Summary: The mean GnRHR ECL2-ELISA OD subjects with documented PCOS were significantly higher than for the control subjects. The sera and IgG purified from sera were active in the GnRHR transfected cells and produced activity increments similar to that observed when the GnRH ligand and the synthetic ligand leuprolide were used instead. A reduction in AAb activity compared to when the GnRHR selective blocker cetrorelix was applied was demonstrated. There was no significant effect of the cetrorelix in the majority of control subjects.

CONCLUSIONS

An ELISA assay for GnRHR AAbs based on a target peptide derived from ECL2 hGnRHR is disclosed. The assay can be used as a diagnostic test for PCOS by detecting GnRHR AAbs. The results show that such autoantibodies are present in a highly significant number of female subjects with clinically documented PCOS compared to the control group.

A subgroup of these subjects was examined by assessing the receptor activation potential of the autoantibody residing in their sera and/or IgG purified from their sera using GnRHR transfected cells. This preparation had a reporter construct that estimates the acute rise in $[Ca^{2+}]_i$ and is quite specific for activation of the overexpressed GnRHR and not to any low-level expression of other GPCRs. A dosage response curve for GnRHR activation in the serum and for purified IgG from the serum was demonstrated. This response was similar to that also observed using the GnRHR specific natural ligand gonadotrophin releasing hormone (GnRH) that normally activates the receptor and also to the response to the synthetic receptor-specific analog leuprolide, which is a potent acute agonist for this receptor. In addition, the GnRHR activity in sera from subjects with elevated GnRHR-AAb activity was blocked using the GnRHR antagonist cetrorelix. This specific receptor blocker allowed for the characterization of the degree of activity observed in the sera measuring the endogenous activity minus the activity following receptor blockade. It was observed that the elevated activity observed in the PCOS subjects is significantly lowered in response to the receptor blockade. Conversely, the majority of control subject activities were not suppressed from their baseline values by this selective antagonist. This supports the concept that there was little if any specific autoimmune activation of the receptor in the control subjects. There were a few elevated values in the "control" subjects that demonstrated some specific inhibitor-sensitive suppression.

As shown above, evidence is provided herein that AAbs directed toward the ECL2 of the GnRHR are significantly elevated in PCOS compared to control infertile but ovulatory women. These autoantibodies will activate the GnRHR and are therefore capable of interacting in vivo both at the hypothalamic and anterior pituitary level. Therefore, they are capable of disrupting the highly regulated and required pulsatile timing required for normal ovulatory function and play a pathogenic role in PCOS. No other Ab directed toward the GnRHR-ECL nor any Ab capable of activating the receptor has previously been reported.

Example 2: GnRHR AAb Binding Peptides

A Mimotope PIN ELISA assay was performed on 11 PCOS subjects and 5 control subjects using sequential GnRHR-ECL2 synthetic peptides, each 8 amino acid residues in length, and each one different from the preceding peptide by addition of the next two C-terminal residues and removal of the last 2 N-terminal residues (see Table 1). The specific peptides were biochemically bonded to the tip of the pin that is attached to the 96 well plate cover in such a fashion that the peptides were immersed in the buffer/sera (1:200) mixture in the well. After incubation, the pins and wells were washed thoroughly, and the well mixture was then replaced by the anti-human-2nd AB (1:10,000) and incubated and washed again; the colorimetric agent was then added. The wells were sequentially counted at 10 min intervals, and values were compared for analysis of O.D. for each pin. The values and pin sequences are shown with time of reading in color code. Results are shown in FIGS. 7-10.

TABLE 1

GnRHR-ECL2 amino acid sequence (SEQ ID NO: 1) and synthetic peptides (SEQ ID NOS: 2-12)

| | |
|---|---|
| DSSGQTKVFSQC*VTHC*SFSQWWHQAFYN | (SEQ ID NO: 1) |
| WWHQAFYN | (SEQ ID NO: 2) |
| SQWWHQAF | (SEQ ID NO: 3) |
| SFSQWWHQ | (SEQ ID NO: 4) |
| HCSFSQWW | (SEQ ID NO: 5) |
| *VTHC*SFSQ | (SEQ ID NO: 6) |
| Q*CVTHC*SF | (SEQ ID NO: 7) |
| FSQC*VTHC* | (SEQ ID NO: 8) |
| KVFSQCVT | (SEQ ID NO: 9) |
| QTKVFSQC | (SEQ ID NO: 10) |
| SGQTKVFS | (SEQ ID NO: 11) |
| DSSGQTKV | (SEQ ID NO: 12) |

Five PCOS subjects with two peaks with a single pin of somewhat lesser activity between them were observed. The O.D. activity for each was >0.8 in each.

Three PCOS subjects were found with a somewhat different pattern. One had two adjacent peaks with very high O.D. values coincident with the N-terminal first of two peaks observed in the five PCOS subjects. The other two had relatively broad reactivity over several of the C-terminal pins with moderate to significant O.D. values. Five control subjects were examined. Two had a single peak coincident with the C-terminal first peak noted in the PCOS. These single peaks were of moderate O.D. activity. Three others had either no peaks or a low activity in the region of the second C-terminal amino acid. The whole sequence of the GnRHR-ECL2 is portrayed as SEQ ID NO:1. Overlapping Peak 1 is SEQ ID NO:8. Overlapping Peak 2 is SEQ ID NO:6.

The use of the L-peptide for each peak or, in certain non-limiting embodiments, the retro-inverso D-amino acid (RID) homolog, can be used to identify which peak is critical for activation of the receptor. Then each peptide separately and/or together will be preincubated with the patient's sera for 30 minutes, and then the mixture used to test for biological activity in the GnRHR transfected cell activity assay. CVTHCSFS (SEQ ID NO:13), comprising portions of SEQ ID NOS: 6-8, is a peptide sequence that could be used to block both epitopes. The RID homologs can be formed in accordance with the disclosure in Patent Application Publication No. US 2016/0222084 (published Aug. 4, 2016; U.S. Ser. No. 14/776,855, filed Sep. 15, 2015), which explains how such retro-inverso D-amino acid homologs can be produced, and which is hereby expressly incorporated herein by reference in its entirety.

Thus, in accordance with the present disclosure, there have been provided compositions, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

REFERENCES

The following references, to the extent that they provide exemplary procedural or other details supplementary to those set forth herein, are specifically incorporated herein by reference. In addition, the following is not intended to be an Information Disclosure Statement; rather, an Information Disclosure Statement in accordance with the provisions of 37 CFR § 1.97 will be submitted separately.

Broekmans F J, Knauff E A, Valkenburg O, Laven J S, Eijkemans M J, Fauser B C. PCOS according to the Rotterdam consensus criteria: Change in prevalence among WHO-II anovulation and association with metabolic factors. BJOG 113(10): p. 1210-7, 2006.

Angela Grassi. Polycystic Ovary Syndrome—Unique Concerns During Pregnancy and Lactation. Today's Dietitian Vol. 10, No. 12, p. 38, 2008.

Maggi R, Cariboni A M, Marelli M M, Moretti R M, Andre V, Marzagalli M, Limonta P. GnRH and GnRH receptors in the pathophysiology of the human female reproductive system. Hum Reprod Update 22(3), 2016.

Patrick R. Gentry, Patrick M. Sexton, Arthur Christopoulos. Novel Allosteric Modulators of G Protein—coupled Receptors. J Biol Chem 290(32): 19478-19488, 2015.

M Gibson-Helm, H Teede, A Dunaif, A Dobras. Delayed diagnosis and a lack of information associated with dissatisfaction in women with polycystic ovary syndrome. Journal of Clinical Endocrinology and Metabolism, published online Dec. 1, 2016.

Li H, Kem D C, Reim S, Khan M, Vanderlinde-Wood M, Zillner C, Collier D, Liles C, Hill M A, Cunningham M W, Aston C E, Yu X. Agonistic Autoantibodies as Vasodilators in Orthostatic Hypotension: A New Mechanism. Hypertension 59(2):402-8, 2012.

Halvorson LM.PACAP modulates GnRH signaling in gonadotropes. Mol Cell Endocrinol 385(1-2):45-55, 2014.

Millar RP1, Babwah A V. KISS1R: Hallmarks of an Effective Regulator of the Neuroendocrine Axis. Neuroendocrinology 101(3):193-210, 2015.

Li H, Zuccolo J, Kem D C, Zillner C, Lee J, Smith K, James J A, Cunningham M W, Yu X. Implications of a vasodilatory human monoclonal autoantibody in postural hypotension. J Biol Chem 288 (42): 30734-41, 2013.

Li H, Kern D C, Zhang L, Huang B, Liles C, Benbrook A, Gali H, Veitla V, Scherlag B J, Cunningham M W, Yu X. Novel retro-inverse peptide inhibitor reverses angiotensin receptor autoantibody-induced hypertension in the rabbit. Hypertension 65(4):793-9, 2015.

Li H, Yu X, Liles C, Khan M, Vanderlinde-Wood M, Galloway A, Zillner C, Benbrook A, Reim S, Collier D, Hill M A, Raj S R, Okamoto L E, Cunningham M W, Aston C E, Kern D C: Autoimmune basis for postural tachycardia syndrome. J Am Heart Assoc 3(1):e000755, 2014.

Li H, Scherlag B J, Kern D C, Benbrook A, Shen X, Cunningham M W, Lazzara R, Aston C E, Yu X: Inducible cardiac arrhythmias caused by enhanced beta 1-adrenergic autoantibody expression in the rabbit. Am J Physiol Heart Circ Physiol 306:H422-428, 2014.

Yu X, Stavrakis S, Hill M A, Huang S, Reim S, Li H, Khan M, Hamlett S, Cunningham M W, Kern D C: Autoantibody activation of beta-adrenergic and muscarinic receptors contributes to an "autoimmune" orthostatic hypotension. J Am Soc Hypertens 6:40-47, 2012.

Li H, Scherlag B J, Kern D C, Benbrook A, Zhang L, Huang B, Cunningham M W, Lazzara R, Yu X: Atrial Tachyarrhythmias Induced by the Combined Effects of beta 1/2-adrenergic Autoantibodies and Thyroid Hormone in the Rabbit. J Cardiovasc Transl Res 7:581-589, 2014.

Duran-Pasten ML1, Fiordelisio-Coll T, Hernandez-Cruz A, Castration-induced modifications of GnRH-elicited $[Ca^{2+}](i)$ signaling patterns in male mouse pituitary gonadotrophs in situ: studies in the acute pituitary slice preparation. BiolReprod 14; 88(2):38, 2013.

Su S, Sun X, Zhou X, Fang F, Li Y. Effects of GnRH immunization on the reproductive axis and thymulin. J Endocrinol 226(2):93-102, 2015.

What is claimed is:

1. A peptide, consisting of:
   6 to 45 amino acids, wherein the 6 to 45 amino acids comprise the amino acid sequence SEQ ID NO:14, at least one D-amino acid upstream of the N-terminal end of SEQ ID NO:14, and at least one D-amino acid downstream of the C-terminal end of SEQ ID NO:14.

2. The peptide of claim 1, wherein the at least one upstream D-amino acid is immediately upstream of the N-terminal end of SEQ ID NO:14, and the at least one downstream D-amino acid is immediately downstream of the C-terminal end of SEQ ID NO:14.

3. A composition comprising:
   a peptide, consisting of
      6 to 45 amino acids, wherein the 6 to 45 amino acids comprise the amino acid sequence SEQ ID NO:14, at least one D-amino acid upstream of the N-terminal end of SEQ ID NO:14, and at least one D-amino acid downstream of the C-terminal end of SEQ ID NO:14; and
   a pharmaceutically-acceptable carrier, vehicle, or diluent in which the peptide is disposed.

4. The composition of claim 3, wherein the at least one upstream D-amino acid is immediately upstream of the N-terminal end of SEQ ID NO:14, and the at least one downstream D-amino acid is immediately downstream of the C-terminal end of SEQ ID NO:14.

5. A peptide conjugate, comprising:
   a peptide, consisting of
      6 to 45 amino acids, wherein the 6 to 45 amino acids comprise the amino acid sequence SEQ ID NO:14, at least one D-amino acid upstream of the N-terminal end of SEQ ID NO:14, and at least one D-amino acid downstream of the C-terminal end of SEQ ID NO:14; and
   a molecule to which the peptide is conjugated, wherein said molecule is selected from the group consisting of polymeric molecules, proteins, polypeptides, antibodies, drugs, imaging agents, labeling agents, radioisotopes, radionuclides, fluorescent labels, chemiluminescent labels, reporter molecules, and diagnostic agents.

6. The peptide conjugate of claim 5, wherein the peptide is conjugated directly to the molecule.

7. The peptide conjugate of claim 5, wherein the peptide is conjugated to the molecule indirectly via a spacer or linker.

8. The peptide conjugate of claim 5, wherein the at least one upstream D-amino acid is immediately upstream of the N-terminal end of SEQ ID NO:14, and the at least one downstream D-amino acid is immediately downstream of the C-terminal end of SEQ ID NO:14.

* * * * *

UNITED STATES PATENT AND TRADEMARK OFFICE
CERTIFICATE OF CORRECTION

PATENT NO. : 11,530,239 B2
APPLICATION NO. : 17/192152
DATED : December 20, 2022
INVENTOR(S) : David C. Kem et al.

Page 1 of 1

It is certified that error appears in the above-identified patent and that said Letters Patent is hereby corrected as shown below:

In the Specification

Column 17, Line 16: Delete "(AMIH)" and replace with -- (AMH) --.

In the References:

Column 22, Line 10: After "Li H," delete "Kern D C," and replace with -- Kem D C, --.

Column 22, Line 18: After "Aston C E," Delete "Kern D C:" and replace with -- Kem D C: --.

Column 22, Line 21: Delete "Kern D C," and replace with -- Kem D C, --.

Signed and Sealed this
Thirty-first Day of January, 2023

Katherine Kelly Vidal
*Director of the United States Patent and Trademark Office*